United States Patent [19]

Takeuchi et al.

[11] Patent Number: 5,162,500

[45] Date of Patent: Nov. 10, 1992

[54] POSTSTATIN AND RELATED COMPOUNDS OR SALTS THEREOF

[75] Inventors: Tomio Takeuchi, Tokyo; Takaaki Aoyagi, Fujisawa; Masa Hamada; Hiroshi Naganawa, both of Tokyo; Keiji Ogawa, Hachioji; Machiko Nagai, Tokyo; Yasuhiko Muraoka, Tokyo; Makoto Tsuda, Tokyo, all of Japan

[73] Assignee: Zaidan Hojin Biseibutsu Kagaku Kenkyu Kai, Tokyo, Japan

[21] Appl. No.: 613,759

[22] PCT Filed: Apr. 13, 1990

[86] PCT No.: PCT/JP90/00491

§ 371 Date: Dec. 7, 1990

§ 102(e) Date: Dec. 7, 1990

[87] PCT Pub. No.: WO90/12805

PCT Pub. Date: Nov. 1, 1990

[30] Foreign Application Priority Data

Apr. 15, 1989 [JP] Japan ............................ 1-094328

[51] Int. Cl.$^5$ .................. A61K 37/02; A61K 37/00; C07K 5/00; C07K 7/00
[52] U.S. Cl. ................................. 530/330; 530/329; 530/331
[58] Field of Search .................. 530/330, 331, 329; 514/19, 18, 17

[56] References Cited

U.S. PATENT DOCUMENTS 4,623,639 11/1986 Hassall et al. .................. 514/18
4,868,155 9/1989 Durette et al. .................. 514/19

FOREIGN PATENT DOCUMENTS 0364344 10/1988 European Pat. Off. .
0363284 4/1990 European Pat. Off. .
50-49492 5/1975 Japan .
60-38399 7/1984 Japan .

OTHER PUBLICATIONS

Hori et al., Peptides: Structure and Function, Editor. Deber et al., pp. 819–822, 1985.

*Primary Examiner*—Lester L. Lee
*Assistant Examiner*—A. M. Davenport
*Attorney, Agent, or Firm*—Nields & Lemack

[57] ABSTRACT

A novel, biologically active substance, poststatin, has been isolated from a culture medium of microorganism belonging to Streptomyces. The novel substance is a peptide compound having a novel structure, wherein the peptide chains have ketone radicals. Thus substance has a high endopeptidase inhibition activity. It is possible to chemically synthesize poststatin related compound having ketone radicals in the peptide chains. These compounds also have an endopeptidase inhibition activity.

4 Claims, 3 Drawing Sheets

POSTSTATIN AND RELATED COMPOUNDS OR SALTS THEREOF

FIELD OF THE INVENTION

The present invention relates to poststatin and related compounds or salts thereof. More specifically, the invention relates to poststatin and related compounds or salts thereof having activities of inhibiting the actions of endopeptidases including those classified as serine enzymes or SH-enzymes. The invention also relates to a process for the preparation of such poststatin compounds, and to a pharmaceutical composition which contains, as active ingredient, the poststatin compounds.

BACKGROUND OF THE INVENTION

Prolylendopeptidase is an example of endopeptidase and exhibits an activity of inactivating the following substances: substance P which is a neuro-conducting substance; thyrotropin-releasing hormone; neurotensin; and vasopressin which seems to have a relation with memories. It is considered that prolylendopeptidase inhibitor substances might have various physiological activities. Particularly, it is observed that a prolylendopeptidase inhibitor substance exhibits an action of inhibiting an inactivation of vasopressin, so that it is expected that this substance might be useful as medicine for the treatment of amnestic syndromes. For instance, Journal of the Japanese Agricultural Chemical Society, 58, 1147-1154 (1984) and Japanese Patent Publication (Laid-open) Nos. 60-172929 (1985) and 60-188317 (1985) disclose that certain prolylendopeptidase inhibitor agents show an anti-amnestic effect. So, it is highly desirable to provide a more effective prolylendopeptidase inhibitor agent which can be used as an anti-amnestic agent.

It is reported by Aoyagi that, from the experimental data concerning the enzyme activity in spleens of NZB/WFl mice sufferring from SLE (systematic lupus erythematosus), it can be said that the amount of prolylendopeptidase increases with a progress of the sick (Journal of Applied Biochemistry, 7, 273-281 (1985)). It is therefore expected that a prolylendopeptidase inhibitor agent might be effective for the treatment of SLE.

It is also known that there are a number of low molecular weight peptidase having an endopeptidase-inhibiting activity. Examples of such low molecular weight peptides are natural peptide aldehydes such as leupeptin and elastatinal. Furthermore, a number of peptide aldehydes have been synthesized as endopeptidase inhibitor agents. According to a theory proposed by Thompson, R. C. (Biochemistry, 12, 47-51 (1973)), such peptide aldehydes are bonded to enzymes, so that the aldehyde radicals of the peptide aldehydes may occupy the sites of the enzymes where they can react with the carbonyl radicals of (substrate) peptide, so as to inhibit the enzyme activity.

Hori et al reported that certain peptides, having an (RS)-3-amino-2-oxo-pentanoic acid ethyl or benzyl ester radical at the C-terminal, can be prepared by a Dakin-West reaction, and that these synthetic peptides inhibit the activity of elastase, which is an example of peptidases (Peptides, Structure and Function, Proceedings of the Ninth American Peptide Symposium, pp. 819-822 (1985)).

DISCLOSURES OF THE INVENTION

As a result of our continuous study on substances which have an endopeptidase-inhibiting activity, we have now found that *Streotomyces viridochromogenes* strain MH534-30F3 produces a substance which strongly inhibits the above-mentioned enzyme. Furthermore, we have succeeded to isolate and purify the inhibitor substance, and have named the substance as poststatin. Poststatin has a novel structure, wherein the peptide chain has ketone radicals, and also has amino acid residues at both terminals thereof. In addition, we have prepared a number of related compounds with reference to the structure of poststatin, and have found that these related compounds also have an endopeptide-inhibiting activity.

Therefore, in the first aspect of the present invention, there are provided poststatin and related compounds or salts thereof having the formula:

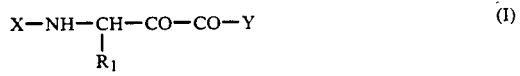

wherein X represents a peptide residue which may have functional radicals optionally protected, or X represents an amino acid residue which may have amino radicals optionally protected, $R_1$ represents a saturated or unsaturated hydrocarbon radical, with the proviso that the steric configuration of a substituent on the carbon atoms, to which the radical $R_1$ is bonded, is the configuration S or RS, and Y represents a peptide residue which may have functional radicals optionally protected, or Y represents an amino acid residue which may have carboxyl radicals optionally protected.

In the second aspect of the invention, there are provided poststatin having the formula:

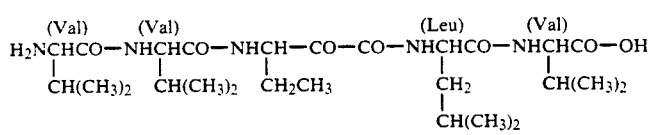

wherein the amino radicals may be present in the protected form, and ester compounds or salts thereof.

In the third aspect of the invention, there is provided a process for the preparation of poststatin of the formula (I) and related compounds or salts thereof, characterized in that a 3-amino-2-hydroxy-fatty acid derivative, having a unit of the formula:

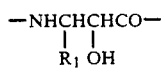

wherein $R_1$ represents a saturated or unsaturated hydrocarbon radical, is oxidized so as to obtain a 3-amino-2-oxo-fatty acid derivative having a unit of the formula:

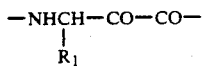

wherein $R_1$ has a meaning stated above, and that the 3-amino-2-oxo-fatty acid derivative thus formed is then optionally subjected to an operation for the removal of the protective radicals and/or to a salt-forming operation.

In the fourth aspect of the invention, there is provided a process for the preparation of a poststatin, characterized in that a poststatin-producing microorganism belonging to Streptomycetaceae is cultured, and that poststatin thus produced is separated from the culture medium.

In the fifth aspect of the invention, there is provided an endopeptidase inhibitor agent comprising, as active ingredient, poststatin or related compounds or salts thereof having the formula (I).

DETAILED EXPLANATION OF THE DRAWINGS:

PREFERRED EMBODIMENTS FOR CARRYING OUT THE INVENTION

Figure 1:
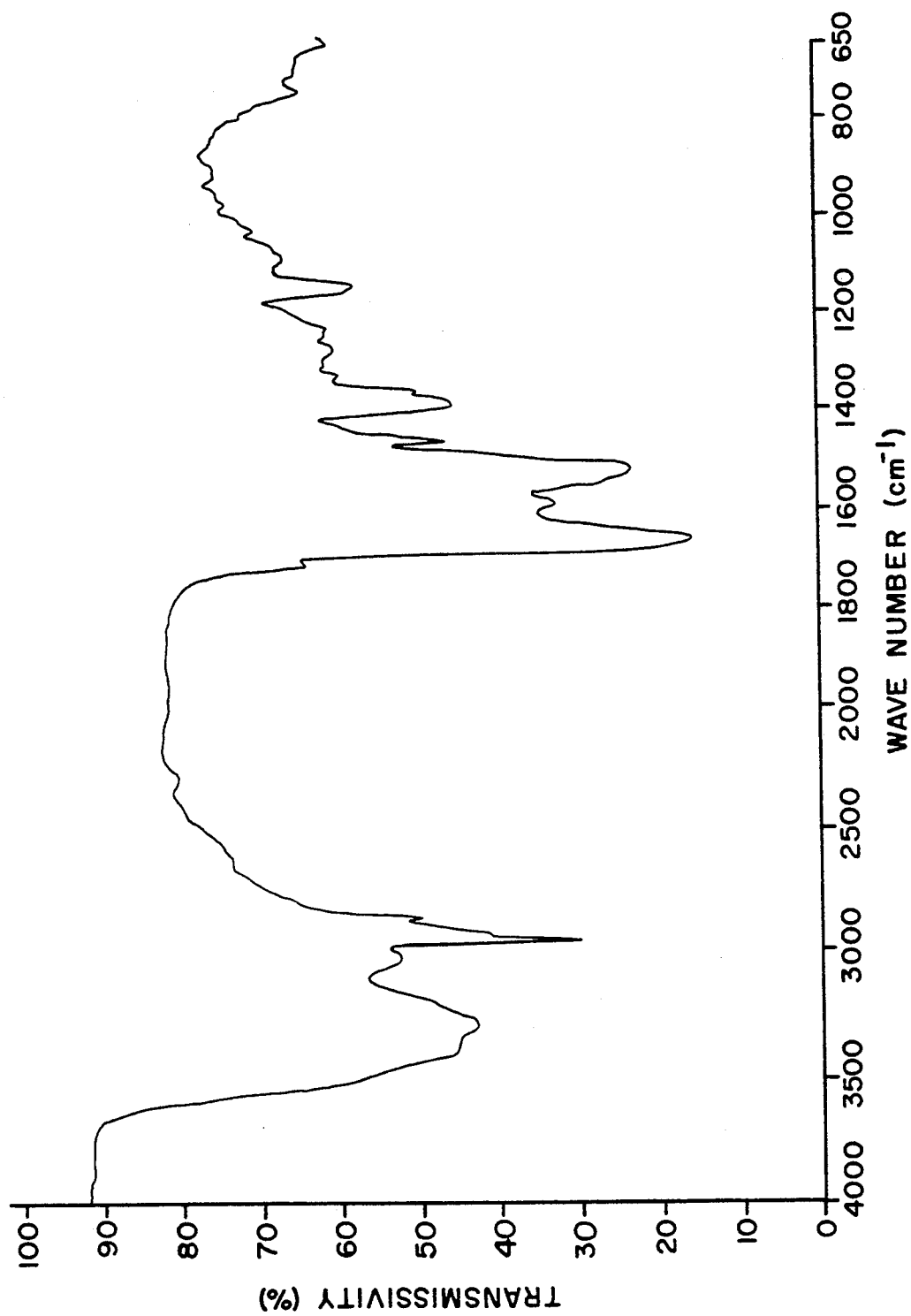
FIG. 1 shows an infrared spectrographic chart of poststatin contained in a potassium bromide tablet.

X and Y in the general formula (I) individually represent an amino acid residue or a peptide residue having amino acid residues. Examples of such amino acid residues are α-amino acid residues, although residues other than α-amino acid residues may also be used.

As examples of α-amino acids, there may be mentioned amino acids of the formula:

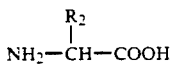

wherein $R_2$ represents hydrogen; or a lower alkyl radical which may be unsubstituted or substituted by amino, hydroxy, mercapto, lower alkylthio, carboxyl, phenyl, hydroxyphenyl, imidazole or indolyl radicals; and amino acids of the formula:

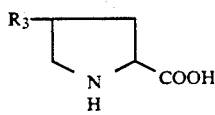

wherein $R_3$ represents hydrogen or hydroxy.

Individual examples of these amino acids are glycine, alanine, valine, leucine, isoleucine, serine, threonine, cysteine, methionine, aspartic acid, glutamic acid, lysine, arginine, phenylalanine, tyrosine, histidine, tryptophan, proline, hydroxyproline and the like. The amino acid residues represented by X are preferably the following amino acid residues (a) to (c) having the amino radicals optionally protected.

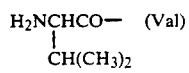 (a)

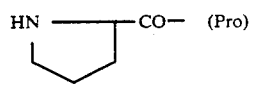 (b)

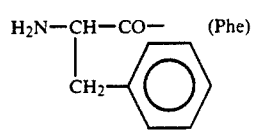 (c)

The amino acid residues represented by Y are preferably the following amino acid residues (a) having the carboxyl radicals optionally protected.

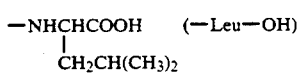 (a)

Examples of peptide residues represented by X or Y are low polymer type peptide residues having about two or three amino acid radicals connected to one another. Preferred examples of peptide residues represented by X are peptide residues (d) to (h) having functional radicals such as amino radicals optionally protected.

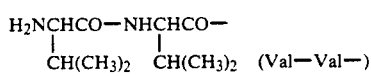 (d)

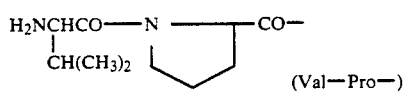 (e)

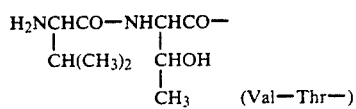 (f)

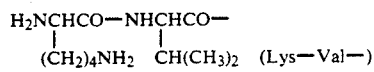 (g)

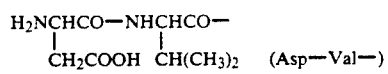 (h)

Preferred examples of peptide residues represented by Y are peptide residues (b) and (c) having functional radicals such as carboxyl radicals optionally protected.

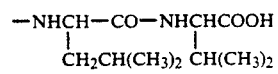 (b)

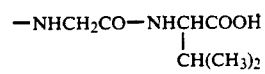 (c)

The protective radicals for the amino acid residues or the amino radicals in peptide residues represented by X or the like include acryl radicals such as phthalyl and sulfonyl radicals; and oxycarbonyl radicals which have a protecting action in the form of urethanes. Examples of acyl radicals are unsubstituted lower alkylcarbonyl, substituted lower alkyl (the substituent may be halogen, nitro, lower alkoxy, phenyl or the like), benzoyl, phthalyl, arylsulfonyl, etc. In the case of phenyl-containing acyl radicals, the phenyl may have a substituent including lower alkyl, halogen, lower alkoxy, nitro and the like. Representative examples of acyl radicals are acetyl, trifluoroacetyl, phenylacetyl, phenylbutanoyl, phenylpropionyl, benzoyl, etc.

Examples of oxycarbonyl radicals, exhibiting a protecting action in the form of urethanes, are unsubstituted lower alkoxycarbonyl, substituted lower alkyloxycarbonyl (the substituents may be those as set forth in the explanation of acyl radicals), for instance, isopropyloxycarbonyl, t-butoxycarbonyl, isopentyloxycarbonyl, substituted benzyloxycarbonyl (the substituents may be those as set forth in the explanation of the acyl radicals), and the like.

In addition to acyl and oxycarbonyl radicals, it is also possible in certain cases to use unsubstituted benzyl, substituted benzyl (the substituents may be those as stated above), o-nitrophenylthio, triphenylmethyl and the like as protective radicals.

As saturated or unsaturated hydrocarbon radicals represented by $R_1$, there may be mentioned saturated or unsaturated lower aliphatic hydrocarbon radicals, aromatic hydrocarbon radicals and the like. They may have substituents. Examples of these radicals are lower alkyl, benzyl, phenyl, etc. Methyl, ethyl, propyl, benzyl and the like are particularly preferred.

As protective radicals for the carboxyl radicals contained in amino acid residues or peptide residues represented by Y or others, it is possible to use, for instance, ester radicals. Examples of such esters are those derived from lower alcohols, benzyl alcohol and the like.

Example of the lower alkyl radicals, used in the invention, are $C_1$-$C_5$ alkyl radicals including methyl, ethyl, propyl, butyl, pentyl and the like.

As the lower alcohols, use may be made of $C_1$-$C_5$ alcohols including methanol, ethanol, propanol, butanol, pentyl alcohol and the like. As the lower alkoxy radicals, it is possible to use $C_1$-$C_5$ alkoxy radicals including methoxy, ethoxy, propoxy, butoxy, etc. As the halogen atoms, there may be mentioned, for instance, fluorine, chlorine and bromine.

Poststatin related compounds of the formula (I) may be present in the form of salts. Examples of such salts are inorganic salts including chlorides, sulfates, nitrates and the like; and organic acid addition salts including p-toluenesulfonates, citrates, succinates and the like. Furthermore, it is also possible to use, for example, salts of alkali metals such as sodium, potassium and the like, and salts of alkaline earth metals including calcium and the like.

Poststain of the formula (I), wherein X is L-valyl-L-valyl, $R_1$ is ethyl, and Y is -D-leucyl-L-valine, may be shown by the chemical formula:

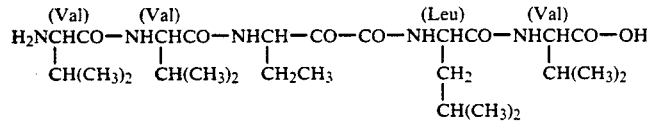

and can be separated from a culture medium containing poststatine-producing microorganism therein.

The physical and chemical properties of poststain are as follows.

(I) Physico-chemical nature of poststatin:
(1) Color and shape: White powder
(2) Elementary analysis:
   C: 55.01%
   H: 8.62%
   N: 12.12%
(3) Molecular weight: 541 (determined on the basis of the peak of mass spectrography)
(4) Molecular formula: $C_{26}H_{47}N_5O_7$ (from the data of mass spectrography, $^{13}$C-NMR spectrometry and elementary analysis); the elementary analytical data showed the presence of $3/2H_2O$.
(5) Melting point: 169°–171° C.
(6) Specific rotation: $[\alpha]_D^{20} + 13.9°$ (c 0.5, acetic acid)
(7) UV-absorption spectra (in 1 mg/ml methanol): weak absorption at about 250 nm.
(8) IR-absorption spectra: see FIG. 1.
(9) H-NMR spectra: see FIG. 2.
(10) C-NMR spectra: see FIG. 3.
(11) Color reactions: On a silica gel thin layer, the compound was "positive" to the following reagents: ninhydrine reagent, Rydon-Smith reagent, 2,3,5-triphenyl tetrazolium chloride reagent and 2,4-dinitrophenylhydrazine reagent.
(12) Solubility: soluble in water, methanol, and dimethyl sulfoxide, and insoluble in acetone, ethyl acetate, chloroform and hexane.
(13) Thin layer chromatography (silica gel "Art. 5715" (Merck); eluant: n-butanol-acetic acid-water (4:1:1); Rf=0.70.
ODS-reversed silica gel (silica gel "Art. 15389" (Merck); eluant: acetonitrile-buffer solution A* (7:13); Rf=0.54 (*The buffer solution A is an aqueous solution containing 5% potassium acetate and 1% citric acid monohydrate).

Poststatin can be obtained by cultivating poststatin-producing bacteria belonging to Streptomycetaceae, and by recovering the aimed poststatin from the culture medium.

As an example of the poststatin-producing microorganism, there may be mentioned a streptomyces, strain MH534-30F3, which has been found by the present inventors in a soil in the ground of the Biseibutsu Kagaku Kenkyusho, Tokyo, Japan. The microbiological properties of strain MH534-30F are as follows.

1. Shape

Under the microscope, it is observed that microorganism of strain MH534-30F3 have branched primary hyphae, and aerial hyphae well grown from the primary hyphae and having a spiral form. No verticillate branches have been observed. The spiral portions are relatively long, often including those with at least 8 fold windings. Matured spores have a shape of ellipse with a size of about 0.5–0.7×0.9–1.1 microns. The spore surfaces are bristly. At least 20 spores form a chain.

2. Growth in culture media

For the identification of colars, use was made of "Color harmony Manual", Container Corporation of America.

(1) Sucrose-nitrate-agar medium (cultivation at 27° C.):

It has been observed that there are aerial hyphae having a color of grayish white (1 dc, Putty) to light greenish grey (24-½ dc), which have been grown on matrices having a color of dark yellowish brown (2 nl, Covert Brown) to grayish yellow brown (3 nl, DK. Brown). The soluble pigments have a brown color.

(2) Glucose-aspagine-agar medium (cultivation at 27° C.)

Matrices have a color of light yellowish brown (3 ie, Camel to 3 l g, Adobe Brown). There are no aerial hyphae. Furthermore, no soluble pigments are found.

(3) Glycerine-asparagine-agar medium (ISP-culture medium 5, cultivation at 27° C.)

There are matrices having a color of grayish yellow brown (2 ie, Lt. Mustard Tan—2 pl, Mustard Brown) to grayish olive (1½—pl, Olive), and aerial hyphae grown on the matrices and having a color of blue (15 ba, Blue Tint) to light bluish gray (19 dc, Aqua Gray—19 fe, Aqua Gray—22 ih, Moss Gray). The rear surfaces of matrices have an olive color. The soluble pigments have a light color of yellow to olive. When HCl is added, the matrices and the soluble pigments make a color shade change so as to have a raddish shade, whereas, when NaOH is added, no color change is made.

(4) Starch-inorganic salt-agar culture medium (ISP-culture medium 4; cultivation at 27° C.)

There are observed aerial hyphae having a color of light bluish gray (19 dc, Aqua Gray—19 fe, Aqua Gray) to light greenish gray (22 in, Moss Gray) and grown on matrices, which are colorless or have a color of light yellow (2 ec, Biscuit). Soluble pigments are not observed.

(5) Tyrosine-agar culture medium (SIP-culture 7; cultivation at 27° C.)

There are observed aerial hyphae having a color of blue (15 ba, Blue Tint) to light greenish gray (22 ih, Moss Gray) and grown on matrices having a color of light brown (3 lg, Adobe Grown) to dark yellowish brown (3 pn, Sepia Brown). Rear surfaces of matrices have an olive tint, and soluble pigments have a faint brown tint. The colors of matrices and soluble pigments will change to reddish when HCl is added thereto. If NaOH is added, there are no color changes of matrices and soluble pigments.

(6) Nutritive agar culture medium (cultivation at 27° C.)

There are observed aerial hyphae having a color faint white and grown on matrices having a color of light yellow (2 ec, Biscuit). Soluble pigments are not observed.

(7) Yeast-malt-agar culture medium (ISP-culture medium 2; cultivation at 27° C.)

There are observed aerial hyphae having a color of light bluish gray (19 dc, Aqua Gray—19 fe, Aqua Gray—22 fe, Bayberry Gray) and grown on Matrices having a color of light yellowish brown (2 ie, Lt. Mustard Tan). Rear surfaces of matrices have an olive tint. No soluble pigments are observed.

(8) Oatmeal-agar-culture medium (ISP-culture medium 3; cultivation at 27° C.)

There are observed aerial hyphae having a color of light bluish gray (19 dc, Aqua Gray) to light greenish gray (22 ih, Moss Gray) and grown on colorless matrices. No soluble pigments are found.

(9) Glycerine-nitrate salt-agar culture medium (cultivation at 27° C.)

There are observed aerial hyphae having a color of grayish white (1 dc, Putty)—light gray (1 fe, Griege)—light brownish gray (93 fe, Silver Gray) and grown on matrices having a color of dark yellowish brown (3 po, Ebony—3 nl, Dk. Brown) to dark olive (1½ pn, Dk. Olivine—1 ml, Dk. Olive Gray). Rear surfaces of matrices have an olive color, and soluble pigments have a faint olive tint. The matrices and the soluble pigments are tinged with brown when HCl is added thereto, whereas NaOH does not cause any color change.

(10) Starch-agar culture medium (cultivation at 27° C.)

There are observed aerial hyphae having a color of light bluish gray (19 fe, Aqua Gray) to light greenish gray 922 ih, Moss Gray) and grown on matrices which are colorless or have a color of light yellow (2 ec, Biscuit). No soluble pigments are found.

(11) Calcium malate-agar culture medium (cultivation at 27° C.)

There are observed aerial hyphae having a color of bluish white to light bluish gray (19 fe, Aqua Gray) and grown on colorless matrices. About 20 days after the start of cultivation, it is observed that soluble pigments have been slightly tinged with brown.

(12) Cellulose culture medium (Filter paper-added synthetic solution; cultivation at 27° C.)

There are observed aerial hyphae having a color of bluish white (19 dc, Aqua Gray) to light bluish gray and thinly grown on colorless matrices. No soluble pigments are found.

(13) Gelatin cultivation

In a simple gelatin cultivation medium (15% gelatin; cultivation at 20° C.), there are observed aerial hyphae having a color of slightly bluish white (22 dc) to light bluish gray (19 fe, Aqua Gray) and grown on colorless matrices. Soluble pigments have a faint brownish tinge. In a glucose-peptone-gelatin culture medium (cultivation at 27° C.), it is observed that no aerial hyphae are grown on colorless matrices, and that soluble pigments have a slightly brownish tinge.

(14) Skimmed milk (cultivation at 37° C.)

It is observed that no aerial hyphae are grown on matrices having a color of light yellow to yellowish brown. No soluble pigments are found.

3. Physiological properties (1) Growth temperatures

A test was made in the following manner. A cultivation was conducted in a glucose-asparagine-agar culture medium (1% glucose, 0.05% asparagine, 0.05% $K_2HPO_4$ and 3.0% agar; pH 7.0) at a temperature of 20° C., 24° C., 27° C., 30° C., 37° C. or 50° C. It was observed that the microorganism had grown at these temperatures except 50° C., although it is considered that a temperature of about 27° to 37° C. is the optimum temperature.

(2) Liquefaction of gelatin culture medium (15% simple gelatin culture medium, cultivation at 20° C.; or glucose-peptone-gelatin culture medium, cultivation at 27° C.)

In the 15% simple gelatin culture medium, a liquefaction is observed after about 14 days from the start of cultivation, although the liquefaction action is very weak. In the glucose-peptone-gelatin culture medium, no liquefaction is observed even after 21 days from the start of the cultivation.

(3) Hydrolysis of starch (starch-inorganic salt-agar cultivation medium, or starch-agar culture medium cultivation at 27° C.)

In both the starch-inorganic-agar culture medium and the starch-agar culture medium, a relatively strong hydrolyzation is observed after about 3 days from the start of the cultivation.

(4) Coagulation and peptonation of skimmed milk (skimmed milk, cultivation at 37° C.)

A very weak coagulation started after about 2 days from the beginning of the cultivation. Before the completion of coagulation, a peptonation begins after about 8 days from the start of the cultivation. The peptonation is completed after about 14 days from the start of the cultivation. This peptonation is strong.

(5) Formation of melanine-like pigments (tryptonyeast-broth culture medium, ISP-culture medium 1; peptone-yeast-Fe-agar culture medium, ISP-culture medium 6; and tyrosine-agar cultivation medium, ISP-culture medium 7; cultivation at 27° C.)

The test results are: "positive" in the tryptone-yeast-broth culture medium and in the peptone-yeast-Fe-agar medium, and "negative" in the tyrosine-agar culture medium.

(6) Availability of carbon source (Pridham-Gottlieb agar medium, ISP-cultivation medium 9, cultivation at 27° C.)

The bacteria grow well by utilising D-glucose, L-arabinose, D-xylose, D-fructose, sucrose, inositol, L-rhamnose, raffinose and D-mannitol.

(7) Dissolving of calcium malate (calcium malate-agar cultivation medium, cultivation at 27° C.)

The test results are "positive".

(8) Nitrate-reducing reactions (aqueous peptone solution containing 0.1% potassium nitrate, ISP-culture medium 8, cultivation at 27° C.)

The test results are "positive".

(9) Decomposition of cellulose (synthetic solution to which filter paper pieces have been added; cultivation at 27° C.)

The test results are "negative".

In summary, it can be said that microorganism of the strain MH534-30F3 have aerial hyphae with a spiral form, and lack verticillate branches. The surfaces of spores are bristly. The microorganism grow in various culture medium and have many aerial hyphae, which are colorless or have a color of light yellow, dark yellow brown or grayish olive. Rear surfaces of matrices have an olive tinge. Soluble pigments are not present, or they are present with a faint brown color. The color of the matrices and the soluble pigments is slightly tinged with red when HCl is added thereto. When NaOH is added, such a color change does not occur. The melanin-like pigments are "positive" in the tryptone-yeast-broth culture medium and the peptone-yeast-iron agar culture medium, and are "negative" in the tyrosine-agar culture medium. The protein-decomposing action is very weak in the gelatin culture medium, but are strong in the skimmed milk culture medium. The starch hydrolyzation action is strong. The cell walls contain LL-2,6-diaminopimelic acid.

In view of the test date described above, it is considered that microorganism of the strain MH534-30F3 belong to Streotomyces. From the prior publications, it is observed that there are the following three kind of known microorganism which are close to MH534-30F3.

*Streotomyces viridochromogenes*

(International Journal of Systematic Bacteriology, 22, 369 (1972); and Soil Science, 8, 163 (1919))

*Streptomyces chartreusis*

(International Journal of Systematic Bacteriology, 18, 95 (1968); and Waksman, The Actionomycetes, Vol. 2, page 192 (1961)) and

*Streptomyces coerulescenes*

(International Journal of Systematic Bacteriology, 18, 100 (1968); and Gauze, Zur Klassifizierung der Actinomyceten, page 93 (1958), veb. Gustav, Fischer Verlag, Jena)

A comparison was made between the above-mentioned three microorganism species and MH534-30F3, and the results thereof are shown in Table 1.

TABLE 1

|  | MH534-30F3 | Streptomyces viridochromogenes IMC S-0674 (ISP5110) | Streptomyces chartreusis IIMC S-0226 (ISP 5085) | Streptomyces coerulescens IMC S-0278 (ISP 5146) |
| --- | --- | --- | --- | --- |
| Aerial hypha | Spiral | Spiral | Spiral | Spiral |
| Spore surface | Bristly | Bristly | Bristly | Bristly |
| Color of aerial hypha | White-light bluish gray-greenish gray | White-light bluish gray | White-light bluish gray | White-light bluish gray |
| Color of matrix | Colorless-light yellow-dark yellowish brown-grayish olive | Colorless-light yellow-brownish gray-dark olive | Colorless-light yellow | Colorless-light yellow |
| Color of rear surface of matrix | Olive tinge | Olive tinge | Same as matrix | Same as matrix |
| Soluble pigment | (−)-Slightly brown tinge | (−)-Brown tinge; olive in ISP-medium 3 | (−)-Slightly yellow tinge | (−)-Slightly brown tinge |
| Color change of pigment with pH | + HCl . . . Reddish tinge + NaOH . . . No change | + HCl . . . Reddish tinge + NaOH . . . No change | + HCl . . . No change + NaOH . . . No change | + HCl . . . No change + NaOH . . . No change |
| Melanine pigment |  |  |  |  |
| ISP-medium 1 | + | + | + | + |
| ISP-medium 6 | + | + | + | + |
| ISP-medium 7 | − | − | − | − |
| Hydrolysis of | + (strong) | + (medium) | + (strong) | + (strong) |

TABLE 1-continued

|  | MH534-30F3 | Streptomyces viridochromogenes IMC S-0674 (ISP5110) | Streptomyces chartreusis IIMC S-0226 (ISP 5085) | Streptomyces coerulescens IMC S-0278 (ISP 5146) |
|---|---|---|---|---|
| starch |  |  |  |  |
| Coagulation of milk | + (very week) | + (strong) | + (very week) | + (week) |
| Peptomation of milk | + (strong) | + (medium) | + (strong) | + (medium) |
| Liquefaction of gelatin |  |  |  |  |
| 15% simple gelatin | + (very week) | + (very week) | + (very week) | + (very week) |
| glucose-peptone-gelatin | − | + (very week) | − | − |
| Reduction reaction of nitrate salt | + | + | + | + |
| Availability of carbon source |  |  |  |  |
| D-glucose | + | + | + | + |
| L-arabinose | + | + | + | + |
| D-xylose | + | + | + | + |
| D-fructose | + | + | + | + |
| sucrose | + | + | + | + |
| inositol | + | + | + | + |
| rhamnose | + | + | + | + |
| raffinose | + | + | + | + |
| D-mannitol | + | + | + | + |

From Table 1, it will be seen that there is a high similarity on properties among MH534-30F3, *Streptomyces viridochromogenes*, *Streptomyces chartreusis* and *Streptomyces coerulescens*.

It is natural that the three species of known microorganism, mentioned above for comparison, are similar to one another. As the characteristic features of *Streptomyces viridochromogenes*, it may be mentioned that rear surfaces of matrices have an olive tinge. In the ISP-culture medium 3, the microorganism produce soluble pigments having a green color. The rear surfaces of matrices and the soluble pigments are tinged with red when HCl is added thereto. These features are disclosed in the above-mentioned publications and also in the article entitled "Streptomyces species comprising the blue-spore series" (Journal of Bacteriology, 85, 676 (1963)). These features are also demonstrated in the above-mentioned comparison test shown in Table 1. In the case of *Streptomyces chartreusis* and *Streptomyces coerulescens*, it is observed that rear surfaces of matrices have not an olive color, and that a pH change does not cause a color change of pigments. Microorganism of the strain MH534-30F3 produce soluble pigments with an olive color in the glycerin-nitrate-agar culture medium, although the microorganism do not produce said pigments in the ISP-3 culture medium. As far as the color of rear surfaces of matrices and the color change caused by the pH change are concerned, microorganism of the strain MH534-30F3 are similar to *Streptomyces viridochromogenes*. However, these two species are different from each other in the coagulation strength of milk and also in the hydrolysis degree of starch. In International Journal of Systematic Bacteriology, 22, 369 (1972), it is disclosed that the results of tests on the formation of melanin-like pigments show "positive" in ISP-culture media 1 and 6, and show "±" in ISP-culture medium 7. However, the results of the practical comparison tests by us are those mentioned above, and the other publications show "positive". Therefore, it is not considered that there is an important problem in this matter.

In consideration of the above-mentioned matters, we have identified the strain MH534-30F as "*Streptomyces viridochromogenes* MH534-30F3".

A sample of the strain MH534-30F was deposited in the Institute of Applied Microbiology, Tokyo, Japan. This sample was assigned Accession No. 9446 (FERM P-9446) on Jul. 2, 1987. This deposit was converted into the international deposit under the Budapest Treaty and renumbered as FERM BP-2848 on Apr. 4, 1990.

The nature of the strain MH534-30F3 is easily changeable, as in the case of other Streptomyces microorganism. For instance, there might be natural or induced mutant microorganism derived from the strain MH534-30F3 or homologs thereof. It is possible, in the process for the production of poststatin according to the invention, to employ all kinds of microorganism of Streptomyces, including those subjected to transductions or gene recombinations, as far as such microorganism are poststatin-producing microorganism.

According to the present invention, the above-mentioned microorganism are grown in a culture medium which contains conventional nutrients employed for microorganisms. As nutrients, use may be made, for instance, of glucose, millet-jelly, dextrine, sucrose, starch, molasses, animal and vegetable oils and fats, and the like. Examples of nitrogen-containing nutrients are soybean powder, embryo buds of wheat, corn steep liquor, cotton seed cake, meat extract, peptone, yeast extract, ammonium sulfate, sodium nitrate, urea, etc. As optional nutrients, it is generally preferred to use inorganic salts which can produce ions of sodium, cobalt, chloride, phosphate, sulfate, etc. It is also possible to use various organic and inorganic substances which can help the growth of microorganism, and which can promote the production of poststatin, which is a physiologically active substance.

For the growth of microorganism, it is suitable to carry out a cultivation method, particularly a deep cultivation method, under aerobic conditions. The cultivation is preferably carried out at a temperature of 15° to 37° C., more preferably a temperature of about 26° to 30° C. The production of poststatin, a physiologically active substance, may depend on culture media and cultivation conditions. In the case of shaking and tank cultivation operations, it can generally be said that the amount of poststatin (which is a physiologically active substance) accumulated will usually arrive at a maximum value after 1 to 10 days from the start of cultivation. When the amount of poststatin, a physiologically active substance, has reached a maximum value in the culture, then the cultivation is stopped, and the culture liquid is subjected to a purification operation to isolate the aimed product.

When a poststatin-containing culture liquid, obtained according to the invention, is purified to obtain the aimed product, it is possible to employ a combination of conventional separation procedures in consideration of the nature of the culture liquid. For instance, the following operations may be effected. A filtered culture liquid is adjusted to pH 5, and then the liquid is passed through a column filled with "Diaion PH-20" (Mitsubishi Kasei Co., Ltd.), washed with water, and subjected to an elution operation with organic solvents such as methanol. The resulting elute is concentrated to dryness under a reduced pressure. The dry substance thus obtained is admixed with a small amount of methanol, and the soluble component-containing portion is passed through a column filled with "Sephadex LH-20" (Pharmacia Co., Ltd.), and subjected to an elution operation with methanol. The resultant elute is concentrated to dryness under a reduced pressure, so that a powdery crude product is obtained.

It is also possible to isolate poststatin by employing a combination of an adsorption chromatography, a gel filtration chromatography and the like. If necessary, such operations may be carried out repeatedly.

In the cultivation steps and the purification steps, it is possible to monitor poststatin by measuring the antiprolylendopeptidase activity. This activity may be determined according to a modified method based on the known method by Tadashi Yoshimoto et al. (Biochim. Biphys. Acta, 569, 184–192 (1979)).

Alternatively, poststatin can be produced by a chemical synthetic process. Also, the homologues of poststatin may be obtained by a similar chemical synthetic process.

Thus, poststatin and related compounds or salts thereof, having the formula (I), can be produced according to a chemical process, wherein a 3-amino-2-hydroxy-fatty acid derivative having a unit of the formula:

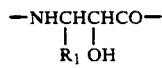
[II]

wherein $R_1$ represents a saturated or unsaturated hydrocarbon radical, is oxidized so as to form a 3-amino-2-oxo-fatty acid derivative having a unit of the formula:

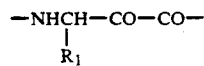
[III]

wherein $R_1$ has the same meaning as stated above, and, if desired, an operation is carried out for removing the protective radicals and/or for forming a salt thereof.

The 3-amino-2-hydroxy-fatty acid derivatives having the unit of the formula (II) may be produced by a known peptide synthetic process employing a 3-amino-2-hydroxy-fatty acid or 3-amino-2-hydroxy-5-aryl-fatty acid as the amino acid reactant. Examples of said compounds are those having the formula:

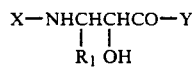
[IV]

wherein X, Y and R have the same meanings as stated above.

Next, an explanation will be given for the present process.

(I) When this process is carried out as a liquid phase process, it may be conducted in the manner shown below.

(1) In this paragraph, a description is given for an embodiment of the process, wherein a catalytic hydrogenolysis operation is carried out for finally removing the protective radicals.

For instance, a benzyl ester of an amino acid represented by Y, or a benzyl ester of a peptide represented by Y is condensed with p-methoxybenzyloxycarbonyl-3-amino-2-hydroxy-fatty acid or t-butoxycarbonyl-3-amino-2-hydroxy-fatty acid or the like in a conventional solvent (e.g., dimethyl formamide) for peptide synthesis in the presence of a conventional condensing agent for peptide synthesis (for instance, carbodiimides or salts thereof, including dicyclohexyl carbodiimide, diisopropyl carbodiimide, N-(3-dimethylaminopropyl)-N'-ethyl carbodiimide and the like) or in the presence of a combination of such a condensing agent and an auxiliary condensing agent (for example, 1-hydroxybenzotriazole, N-hydroxy-succinic acid imide or the like). Then, the p-methoxybenzyloxycarbonyl radical or the t-butoxycarbonyl radical is removed by employing an agent for selectively removing the protective radical, for instance, trifluoroacetic acid. Thereafter, amino acids or peptides represented by X are successively condensed in a conventional manner so as to produce the aimed product.

(2) In this paragraph, an explanation is made about a synthetic process, wherein trifluoroacetic acid is used for the final removal of protective radicals.

For instance, a t-butyl ester of amino acid represented by Y or a t-butyl ester of peptide represented by Y is condensed with a p-methoxybenzyloxycarbonyl-3-amino-2-hydroxy-fatty acid or a benzyloxycarbonyl-3-amino-2-hydroxy-fatty acid in a manner similar to that mentioned in method (1). Next, a catalytic hydrogenolysis operation is carried out to remove the protective radicals for amino radicals, e.g. p-methoxybenzyloxycarbonyl or benzyloxycarbonyl radicals. Thereafter, amino acids or peptides represented by X shown in the formula (I) may be successively condensed.

(II) When the present process is to be conducted in a solid phase, the process can be carried out, for instance, in the following manner.

As the starting material, use may be made of a 9-fluorenyl-methyloxycarbonyl-aminoacyl-p-alkoxybenzylalcohol resin. The 9-fluorenylmethyloxycarbonyl radicals are removed by a treatment with a base. Condensation reactions are successively conducted by employing 9-fluorenylmethyloxycarbonyl-amino acids, 9-fluorenylmethyloxycarbonyl-3-amino-2-hydroxypentanoic acid and then employing 9-fluorenylmethyloxycarbonyl-amino acids. Finally, benzyloxycarbonyl-amino acids, t-butoxycarbonylamino acids or appropriate carboxylic acids are condensed for providing protective radicals for the amino radicals.

The resultant 3-amino-2-hydroxy-fatty acid derivative, having the unit of the formula (II), such as a compound represented by the general formula (IV), is then oxidized under such a mild condition that no influence is given on the other peptide moieties. The oxidation reaction may be carried out, for instance, by employing a combination of (1) dimethyl sulfoxide, (2) a catalyst, e.g., pyridine-trifluoro acetate and (3) a carbodiimide or acetic acid anhydride. The oxidation reaction is preferably conducted in the dimethyl sulfoxide solvent or in another inert solvent at a temperature of about 0° to 40° C. for about 3 to 48 hours. By this oxidation reaction, it is possible to produce a 3-amino-2-oxo-fatty acid derivative, having the unit of the formula (III). If necessary, this derivative may be subjected to an operation for wholly or partially removing the protective radicals, whereby a compound of the formula (I) may be obtained.

Next, a description is given for the optional step of removing the protective radicals.

For instance, in the case of 3-amino-2-oxo-fatty acid derivatives having a unit of the formula (III), e.g., compounds of the formula (I), if X or Y is a hydroxy-containing amino acid radicals, such as a serine or threonine radical protected in the form of t-butyl-ether, then an operation for finally removing the protective radicals is usually effected by using trifluoroacetic acid. If a catalytic hydrogenolysis operation is carried out for finally removing the protective radicals, then the hydroxyl radicals, contained in the amino acid such as serine or threonine, may be protected in the form of benzyl ether.

If desired, poststatin and related compounds thereof may be converted into salts in a conventional manner. For instance, poststatin or derivatives thereof may be treated with a solution of inorganic or organic acids, or a solution of potassium or sodium hydroxide or the like.

Poststatin and related compounds or salts thereof according to the invention have an endopeptidase-inhibiting activity. Particularly, in the case of poststatin and related compounds thereof having the formula (I), wherein Y is -D-leucine, -D-leucyl-valine or an ester radical thereof, it is observed that these compounds have a high prolylendopeptidase-inhibiting activity. In the case of poststatin derivatives of the formula (I), wherein X is a valyl-valyl radical having a terminal amino radical optionally protected, $R_1$ is an ethyl radical, and Y is an L-leucyl-valine radical, a glycyl-valine radical or a corresponding ester radical, they have a high cathepsin B-inhibiting activity.

The compounds according to the invention have a low toxicity. In the case of mice, $LD_{50}$ (i.v.) of poststatin is at least 200 mg/kg. Therefore, it can be expected that the compounds according to the invention will be useful, for instance, as a drug for treating amnesia and autoimmune diseases including systemic erythematosus and the like.

Poststatin and related compounds or salts thereof may usually be administered orally or parenterally, for instance, intravenously, subcutaneously and intramuscularly. The dose will be varied, depending on the state of patients, administration manner, etc. Usually, the dose is 0.5-200 mg/kg/day, preferably 1-100 mg/kg/day.

The active compounds can be administered in the form of conventional formulations. In the case of oral administrations use may be made of tablets, granules, capsules, etc. In the case of parenteral administrations, use may be made, for instance, of formulations for injections, which have been usually prepared with physiological sodium chloride solutions, resolvents, etc.

In the present specification, the following abbreviations are used.
Val: valine;
Pro: proline;
Asp: aspartic acid;
Phe: phenylalanine
Leu: leucine;
Gly: glycine;
Lys: lysine;
Thr: threonine;
Z: benzyloxycarbonyl;
Boc: t-butoxycarbonyl;
PB: phenylbutanoyl;
PP: phenylpropionyl;
PA: phnylacetyl;
Bz: benzoyl;
OBZl: benzyl ester;
OBut: t-butyl ester;
OMe: methyl ester;
Fmoc: 9-fluorenylmethyloxycarbonyl;
HOBt: 1-hydroxy-benzotriazole;
EtAhp: 3-amino-2-hydroxy-pentanoic acid.

The invention will be illustrated in detail by Examples.

EXAMPLE 1

Biological production of poststatin (compound 1) employing poststatin-producing microorganism As the culture medium for initial cultivation and for large scale cultivation, use was made of a culture medium containing 1.0% bactosoytone, 2.0% galactose, 0.5% corn steep liquor, 2.0% dextrin, 0.2% ammonium sulfate and calcium carbonate. Before a sterilization operation, the medium was adjusted to pH 7.4.

110 ml of the initial culture medium were supplied to a 500 ml Erlenmeyer flask, and subjected to a sterilization treatment at 120° C. for 20 minutes. The culture medium was inoculated with 1 or 2 platinum loop volumes of *Streptomyces viridochromogenes* MH534-30F3 (FERM P-9446) which had been grown by a slant cultivation.

Each of other 500 ml flasks was charged with 110 ml of the production medium, which were sterilized at 120° C. for 20 minutes. The production medium was inoculated with 2 ml of the seed medium, and a shaking cultivation was effected at 27° C. for 4 days. After the cultivation, a filtration operation was carried out by employing diatomaceous earth as the filter aid, so that a solid-containing residue and a filtrate (i.e. cultivation filtrate) were obtained.

12.5 l of the cultivation filtrate were adjusted to pH 5 by adding hydrochloric acid thereto. Thereafter, the cultivation filtrate was passed through a column filled with 1 l of a commercial adsorption resin "Diaion HP-20", then washed with water, and subjected to an elution operation with 80% methanol (2 l). The resulting eluate, which involved the active ingredient-containing fractions, was concentrated under a reduced pressure, whereby 8 g of a poststatin-containing brown powder product were obtained.

The resultant powder was admixed with a small amount of methanol, and the soluble component-containing solution thus obtained was subjected to a chromatography, wherein use was made of a 1 liter column filled with "Sephadex LH-20" (Pharmacia Co., Ltd.), and methanol as the eluant. Fractions, each having a weight of 15 g, were obtained. The active fractions Nos. 20-27 were concentrated under a reduced pressure, so that 1.5 g of light brown powder were obtained.

The powder just mentioned above was dissolved in a small amount of 22% acetonitrile, and subjected to an reverse phase silica gel chromatography, using a 1 l column filled with 22% acetonitrile and an reverse phase silica gel ("YMC-Gel ODS60A 60/200 mesh", manufactured by Koyama Yamamura Kagaku Kenkyusho Co., Ltd.), and also using 22% acetonitrile as the eluant. Fractions, each having a weight of 15 g, were obtained. The active fractions Nos. 30-80 were concentrated under a reduced pressure, so that 200 mg of poststatin-containing yellow powder were obtained.

The powder thus obtained was dissolved in 4 ml of a buffer solution A which contained acetonitrile-5% potassium acetate, and 1% citric acid monohydrate (9:4). The resulting solution was filtered by using a millipore filter ("FILTER UNITMILLEX-SR", 0.5 μm, manufactured by Millipore Co., Ltd.), and the filtrate was subjected to a purification operation by means of a high speed liquid chromatography ("Nucleosil$_5$-C$_{18}$-column", 20 φ×300 mm, manufactured by Senshu Kagaku Co., Ltd.). A mixture of acetonitrile and buffer solution A (9:41) was used as the mobile phase at a flow rate of 8 ml/min. Fractions, each having a volume of 8 ml, were obtained. The active fractions No. 52-60 were distilled to remove the acetonitrile therefrom, and then diluted with water to a total volume of 200 ml. The resulting aqueous solution was passed through a column (920 ml) filled with "Diaion HP-20", which had been equilibrated with water. The column was washed with water, and the elution was effected with 80% methanol. The eluate, containing the active fractions, was concentrated under a reduced pressure to obtain 20 mg of a light yellow powder product which contained poststatin.

Figure 2:
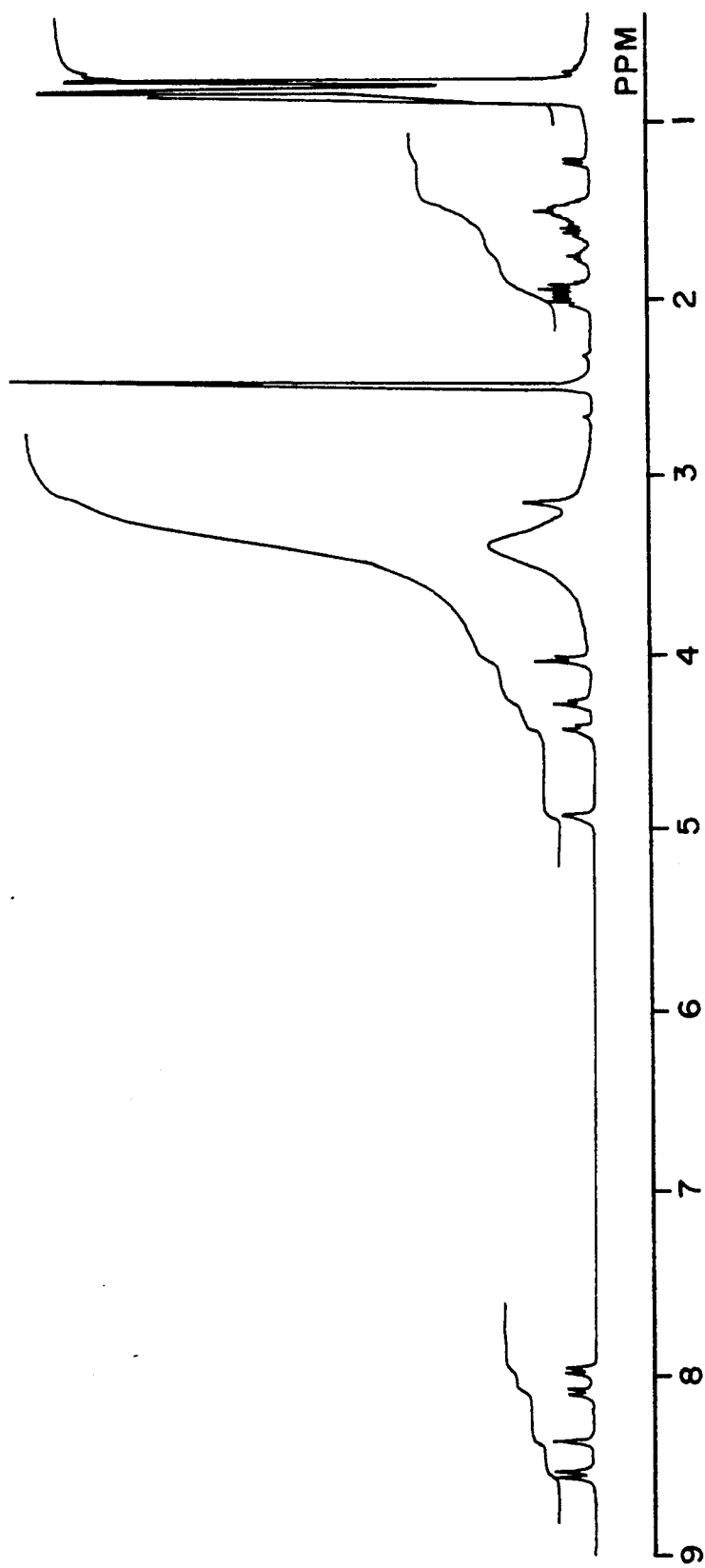
FIG. 2 shows an H-NMR spectrographic chart (400 MHZ) of poststatin measured in deuterium-containing dimethyl sulfoxide.
Figure 3:
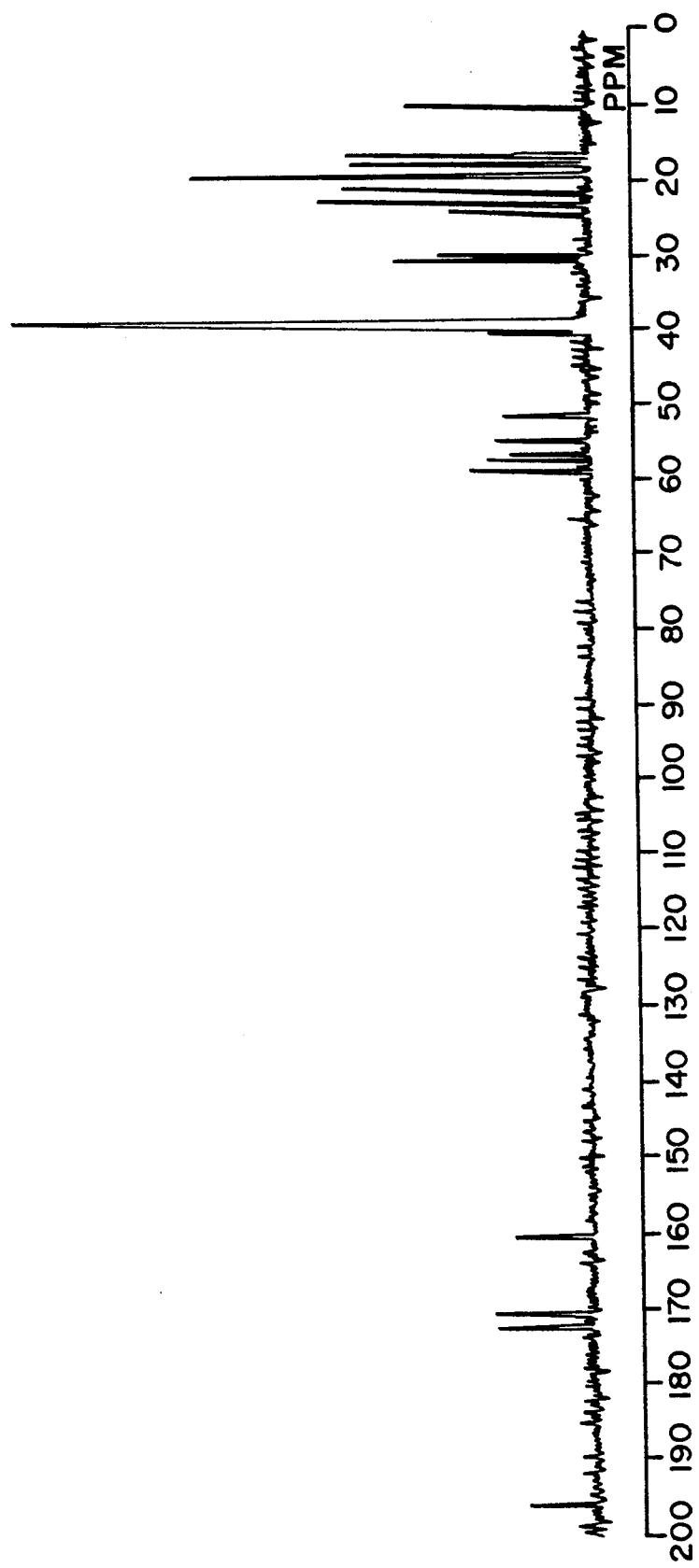
FIG. 3 shows a C-NMR spectrographic chart (100 MHZ) of poststatin measured in deuterium-containing dimethyl sulfoxide.

The poststatin-containing powder thus obtained was dissolved in a small amount of methanol and the resultant solution was allowed to stand at 4° C. for 20 days. The precipitate thus formed was separated by filtration with a glass filter, so that 15 mg of pure poststatin were obtained as white powder, which has a melting point of 169°-171° C. The infra-red spectral data, the H-nuclear magnetic resonance spectral data and the C-nuclear magnetic resonance spectral data of the pure poststatin are shown in FIGS. 1, 2 and 3, respectively.

REFERENCE EXAMPLE 1

Synthesis of Boc-D-leucyl-L-valine benzyl ester 0.749 g (3.00 mmol) of Boc-D-leucine monohydrate, 1.252 g (3.30 mmol) of L-valine benzyl ester p-toluenesulfonate and 0.811 g (6.00 mmol) of N-hydroxybenzotriazole were dissolved in 15 ml of dichloromethane. The resulting mixture was cooled with ice, and admixed with 0.504 ml (3.60 mmol) of triethylamine and 1.108 g (4.20 mmol) of 97% 1-ethyl-3-(3-dimethylaminopropyl)carbodiimide perchlorate. The reaction mixture was stirred for 2 hours, and then further stirred at room temperature for 4 hours. After the completion of the reaction, 30 ml of water and 5 ml of a 1% aqueous citric acid solution were added to the reaction mixture. The crystals thus deposited were filtered off. The organic layer successively was washed with 20 ml of water, 20 ml of a saturated aqueous sodium hydrogen carbonate solution and 10 ml of water, dried over anhydrous sodium sulfate, and distilled to remove the solvent therefrom, whereby 1.390 g of crude Boc-D-leucyl-L-valine benzyl ester product were obtained as white crystals.

Next, the crude crystalline product was purified by a column chromatography (silica gel, ethyl acetate:hexane (5:2)), so that 1.233 g of Boc-D-leucyl-L-valine benzyl ester were obtained as white crystals. Yield: 97.8%; mp.; 82.0°-83.0° C.; $[\alpha]_{DD}^{29}+35.1°$; $[\alpha]_{436}^{29}+76.6°$ (c 1.02, chloroform).

$^1$H-NMR (CDCl$_3$)

δ 0.85, 0.92(d, d, 3H, 3H, J=7 Hz, CH$_3$);
0.90-0.98(d, d, 3H, 3H, J=2.7 Hz, ch$_3$);
1.36-1.54(m, 10H, (CH$_3$)$_3$COCO, (CH$_3$)$_2$CH-CH$_a$H$_b$);
1.62-1.76(m, 2H, (CH$_3$)$_2$CH-CH$_a$H$_b$);
2.14-2.27(m, 1H, (CH$_3$)$_2$CHCH);
4.14(br, 1H, NHCHCONH);
4.57(dd, 1H, J=9.2, 4.2 Hz, CONHCHCOO);
4.79(br, 1H, NH);
5.13, 5.19(d, d, 1H, 1H, J=12.0 Hz, CH$_2$Ph);
6.68(br, 1H, NH);
7.29-7.40(m, 5H, pH).

PREFERENCE EXAMPLE 2

Synthesis of Boc-D-leucyl-L-valine benzyl ester

The procedures shown in Reference Example 1 were repeated, except that 0.693 g (6.02 mmol) of N-hydroxysuccinic acid imide was used instead of N-hydroxybenzotriazole. Boc-D-leucyl-L-valine benzyl ester was obtained in an amount of 0.710 g.

REFERENCE EXAMPLE 3

Synthesis of threo(2R, 3S),(2S, 3R)-3-(p-methoxybenzyloxycarbonyl)amino-2-hydroxy-pentanoic acid 5.99 g (45.0 mmol) of threo(2R, 3S),(2S, 3R)-3-amino-2-hydroxy-pentanoic acid were mixed with 15.07 g (49.5 mmol) of S-4,6-dimethylpyrimidin-2-yl-thiolcarboxylic acid p-methoxybenzyl ester, 25 ml of water, 25 ml of dioxane and 9.45 ml (67.5 mmol) of triethylamine, and the resultant reaction mixture was stirred at room temperature for 24 hours. After the completion of the reaction, the reaction mixture was admixed with 65 ml of water, and washed twice with 100 ml of ethyl acetate. The aqueous layer was cooled on an ice bath, and admixed with 22 ml of 5N hydrochloric acid to adjust to pH 2. The aqueous layer was extracted once with 65 ml of ethyl acetate, and then twice with 30 ml of ethyl acetate. The oil layer was washed three times with 50 ml of 5% hydrochloric acid and twice with 50 ml of a saturated aqueous sodium chloride solution, dried over anhydrous sodium sulfate, and distilled to remove the solvent therefrom. 9.65 g of threo(2R, 3S),(2S, 3R)-3-(p-methoxybenzyloxycarbonyl)amino-2-hydroxy-pentanoic acid were obtained. Yield: 72.1%.

The starting material, namely threo-3-amino-2-hydroxypentanoic acid can be produced by a process, wherein optically inert 3-amino-2-hydroxy-pentanoic acid is dissolved in an ethanol-water solvent, and the threo form is separated from the erythro form by utilizing the solubility difference.

REFERENCE EXAMPLE 4

Synthesis of erythro(2R, 3S),(2S, 3R)-3-(p-methoxybenzyloxy-carbonyl)amino-2-hydroxy-pentanoic acid The procedures of Reference Example 3 were repeated, except that 5.99 g (45.0 mmol) of erythro(2R, 3S),(2S, 3R)-3-amino-2-hydroxy-pentanoic acid were used instead of threo(2R, 3S),(2S, 3R)-3-amino-2-hydroxypentanoic acid employed in Reference Example 3. 10.76 g of erythro(2R, 3S),(2S, 3R)-3-(p-methoxy-benzyloxycarbonyl)amino-2-hydroxypentanoic acid were obtained.

REFERENCE EXAMPLE 5

Synthesis of Z(OMe)-(2R, 3S)-3-amino-2-hydroxy-pentanoyl-D-leucyl-L-valine benzyl ester 189.2 mg (0.450 mmol) of Boc-D-leucyl-L-valine benzyl ester were admixed with 2 ml of trifluoroacetic acid. The mixture thus obtained was stirred at room temperature for 40 minutes, and distilled to remove the solvent therefrom. The residue was admixed with 2 ml of toluene, and the resulting solution was distilled to remove the solvent therefrom. The mixing/distillation operation was conducted twice, so that D-leucyl-L-valine benzyl ester trifluoroacetate was obtained as white crystals.

This compound was mixed with 133.8 mg (0.450 mmol) of (2R, 3S)-3-(p-methoxy-benzyloxycarbonyl)amino-2-hydroxy-pentanoic acid, 91.2 mg (0.675 mmol) of N-hydroxy-benzotriazole and 2 ml of DMF. The resulting reaction mixture was cooled with ice, and admixed with 50.4 μl (0.450 mmol) of N-methyl-morpholine and 148.3 mg (0.563 mmol) of 97% 1-ethyl-3-(3-dimethylaminopropyl)carbodiimide perchlorate, stirred for 2 hours, and further stirred at room temperature overnight.

After the completion of the reaction, the reaction mixture was diluted with 30 ml of dichloromethane, washed successively with 10 ml of a 1% aqueous citric acid solution, 10 ml of water, 10 ml of a saturated aqueous sodium hydrogen carbonate solution and 10 ml of water, dried over anhydrous sodium sulfate and distilled to remove the solvent therefrom. 316.5 mg of crude Z(OMe)-(2R, 3S)-3-amino-2-hydroxy-pentanoyl-D-leucyl-L-valine benzyl ester were obtained as oil. The crude product was purified by a column chromatography (silica gel, ethyl acetate:hexane (5:1)), so that 197.6 mg of Z(OMe)-(2R, 3S)-3-amino-2-hydroxy-pentanoyl-D-leucyl-L-valine benzyl ester were obtained as white crystals. Yield: 73.2%; mp.: 115.0°–115.5° C.; $[\alpha]_D^{25}+45.5°$; $[\alpha]_{346}^{25}+102.9°$ (c 1.04 chloroform).

$^1$H-NMR (CDCl$_3$)

δ 0.80–1.04(m, 15H, CH$_3$x5);
1.51–1.80(m, 5H, CH$_2$x2, CH(Leu));
2.19(m, 1H, CH(Val));
3.70–3.85(m, 4H, CH$_3$O, CH(EtAhp));
4.12(dd, 1H, J=6.4, 3.0 Hz, CHOH);
4.52(dd, 1H, J=8.4, 4.8H$_2$, CH(Val));
4.49(m, 1H, CH(Leu));
4.61(br d, 1H, J=6.4 Hz, OH);
4.98(s, 2H, CH$_2$-C$_6$H$_4$);
5.08, 5.18(d, d, 2H, J=12.4 Hz, CH$_2$Ph);
5.31(br, d, 1H, J=8.4 Hz, NH(EtAhp));
6.79(br, d, 1H, J=8.4 Hz, NH(Val));
6.84–6.92(m, 2H, C$_6$H$_4$);
7.07(br, d, 1H, J=8.4 Hz, NH(Leu));
7.22–7.40(m, 7H C$_6$H$_4$, Ph).

The starting substance, namely (2R, 3S)-3-(p-methoxy-benzyloxycarbonyl)-amino-2-hydroxy-pentanoic acid can be produced by a process, wherein the threo form, shown in Example 3, is admixed with (-)-1-(1-naphthyl)ethylamine, the resulting mixture is dissolved in ethanol under heating, the solution thus formed is allowed to stand at room temperature to precipitate a crystalline substance, which is then separated by filtration. The crystalline substance is purified and recrystallized, and decomposed with 0.5N hydrochloric acid. The decomposition product is extracted with ethyl acetate, dried over anhydrous sodium sulfate, and distilled to remove the solvent therefrom, so that the above-mentioned starting compound is obtained.

REFERENCE EXAMPLE 6

Synthesis of Boc-L-valyl-(2R, 3S)-3-amino-2-hydroxypentanoyl-D-leucyl-L-valine benzyl ester To 190.2 mg (0.317 mmol) of Z(OMe)-(2R, 3S)-3-amino-2-hydroxy-pentanoyl-D-leucyl-L-valine benzyl ester were added 0.1 ml of anisole and 2 ml of trifluoroacetic acid. The resulting mixture was stirred at room temperature for 40 minutes, and distilled to remove the solvent therefrom. The residue was admixed with 2 ml of toluene, and distilled to remove the solvent therefrom. The admixing/distillation operation as mentioned above was effected twice, whereby 243.6 mg of (2R, 3S)-D-leucyl-L-valine benzyl ester trifluoroacetate were obtained.

219.2 mg (about 0.285 mmol) of the salt thus obtained were admixed with 65.4 mg (0.301 mmol) of Boc-L-valine, 58.1 mg (0.430 mmol) of N-hydroxylbenzotriazole and 2 ml of DMF to form a solution. The solution was cooled with ice and admixed with 32 μl (0.286 mmol) of N-methylmorpholine and 94.0 mg (0.357 mmol) of 97% 1-ethyl-3-(3-dimethylaminopropyl)carbodiimide perchlorate. The reaction mixture was stirred for 2 hours, and further stirred at room temperature overnight. After the completion of the reaction, the reaction mixture was diluted with 30 ml of dichloromethane, successively washed with 10 ml of a 1% aqueous citric acid solution, 10 ml of water, 10 ml of a saturated aqueous sodium hydrogen carbonate solution and 10 ml of water, dried over anhydrous sodium sulfate, and distilled to remove the solvent therefrom. 520.8 mg of crude Boc-L-valyl-(2R, 3S)-3-amino-2-hydroxypentanoyl-D-leucyl-L-valine benzyl ester were obtained as oil.

The crude product was purified by a column chromatography (silica gel, dichloromethane:methanol (24:1)), so that 149.7 mg of Boc-L-valyl-(2R, 3S)-3-amino-2-hydroxy-pentanoyl-D-leucyl-L-valine benzyl ester were obtained as white crystals. Yield: 82.8%; mp.: 167.0°–168° C.; $[\alpha]_D^{26}+35.7°$; $[\alpha]_{436}^{26}+81.0°$ (c 1.00, chloroform).

$^1$H-NMR (CDCl$_3$)

δ 0.80–1.03(m, 21H, CH$_3$x7);
1.44(S, 9H(CH$_3$)$_3$COCO);
1.52–1.90(m, 5H, CH$_2$x2, CH(Leu));
2.11(m, 1H, CH(Val));
2.19(m, 1H, CH(Val)),
3.87(m, 1H, CHNH(EtAhp));
3.93(dd, 1H, J=5.8, 8.5 Hz, CH(Val));
4.10(dd, 1H, J=3.4, 7.0 Hz, CHOH);

4.36(m, 1H, CH(Leu));
4.58(dd, 1H, J=5.0, 8.6 Hz, CH(Val));
5.09(br, 1H, NH(Val));
5.10, 5.20(d, d, 2H, J=12.2 Hz, CH$_2$Ph);
5.36(br, 1H, OH);
6.98(br, d, 1H, J=8.6 Hz, NH(Val));
7.04(br, d, 1H, J=8.4 Hz, NH(EtAhp));
7.20(br, d, 1H, J=8.4 Hz, NH(Leu));
7.30–7.40(m, 5H, pH).

REFERENCE EXAMPLE 7

Synthesis of Z-L-valyl-L-valyl-(2R, 3S)-3-amino-2-hydroxypentanoyl-D-leucyl-L-valine benzyl ester 145.0 mg (0.228 mmol) of Boc-L-valyl-(2R, 3S)-3-amino-2-hydroxypentanoyl-D-leucyl-L-valine benzyl ester were admixed with 2 ml of trifluoroacetic acid. The resultant solution was stirred at room temperature for 40 minutes, and distilled to remove the solvent. The residue was mixed with 2 ml of toluene, and then the solvent was distilled off. The mixing/distillation operation was effected twice to obtain L-valyl-(2R, 3S)-3-amino-2-hydroxy-pentanoyl-D-leucyl-L-valine benzyl ester trifluoroacetate as white crystals.

The salt thus obtained was mixed with ethyl acetate to obtain 10 ml of a mixture. 1 ml of this mixture was taken out as a sample, and the remaining mixture was distilled to remove the solvent therefrom. The residue (0.206 mmol) was admixed with 54.8 mg (0.218 mmol) of Z-L-valine, 42.4 mg (0.314 mmol) of N-hydroxybenzotriazole and 1.5 ml of DMF to form a solution. The solution was cooled with ice, and admixed with 23 μl (0.206 mmol) of N-methylmorpholine and 68.0 mg (0.258 mmol) of 97% 1-ethyl-3-(3-dimethylamino-propyl)carbodiimide perchlorate. The resulting reaction mixture was stirred for 2 hours, and further stirred at room temperature overnight. After the completion of the reaction, the reaction mixture was diluted with 15 ml of dichloromethane, successively washed with 7 ml of a 1% aqueous citric acid solution, 7 ml of water, 7 ml of a saturated aqueous sodium hydrogen carbonate solution and 7 ml of a saturated sodium chloride solution, dried over anhydrous sodium sulfate, and distilled to remove the solvent. 277.9 mg of crude Z-L-valyl-L-valyl-(2R, 3S)-3-amino-2-hydroxy-pentanoyl-D-leucyl-L-valine benzyl ester were obtained as an amorphous substance having partially crystallized portions.

The crude substance thus produced was purified by a column chromatography (silicagel, dichloromethane:-methanol (40:1)) to obtain 125.9 mg of Z-L-valyl-L-valyl-(2R, 3S)-3-amino-2-hydroxy-pentanoyl-D-leucyl-L-valine benzyl ester as white crystals. Yield: 79.7%; mp.: 222.0°–223.0° C.; $[\alpha]_D^{27}+9.2°$; $[\alpha]_{436}^{27}+24.4°$ (c 1.01, chloroform).

SI-MS: m/Z768(M+1+); 790(M+Na+).

$^1$H-NMR (CDCl$_3$)

δ 0.76–1.00(m, 27H, CH$_3$x9);
1.37(m, 1H, CH$_3$-CH$_a$H$_b$);
1.53–1.85(m, 4H, (CH$_3$)$_3$CHCH$_2$, CH$_3$H$_a$H$_b$);
1.93–2.10(m, 2H, CHx2(Val));
2.17(m, 1H, CH(Val));
4.13–4.27(m, 2H, NHCHCH(OH)CO);
4.41–4.64(m, 4H, CHx3(Val), CH(Leu));
5.06, 5.15(d, d, 2H, J=12.0 Hz, COOCH$_2$Ph);
5.06, 5.09(d, d, 2H, J=12.0 Hz, PhCH$_2$OCO);
5.49(br, s, 1H, OH);
5.86(br, 1H, NH(Val));
7.09(br, 1H, NH(Val));
7.22(br, 1H, NH(EtAhp));
7.22–7.39(m, 10H, Phx2);
7.45(br, d, 1H, J=7.8 Hz, NH(Leu));
7.94–8.23(br, 1H, NH(Val)).

EXAMPLE 2

Synthesis of 2-L-valyl-L-valyl-(3S)-3-amino-2-oxo-pentanoyl-D-leucyl-L-valine benzyl ester (compound 2)

106.8 mg (0.141 mmol) of Z-L-valyl-L-valyl-(2R, S)-3-amino-2-hydroxypentanoyl-D-leucyl-L-valine benzyl ester were admixed with 19.9 mg (0.103 mmol) of pyridine trifluoroacetate, 116.2 mg (0.441 mmol) of 97% 1-ethyl-3-(3-dimethylamino-propyl)carbodiimide perchlorate, 0.5 ml of DMSO and 2 ml of benzene to form a solution, which was then stirred at room temperature for 24 hours. After the completion of the reaction, the reaction mixture was diluted with 15 ml of ethyl acetate, washed with 5 ml of water, dried over anhydrous sodium sulfate and distilled to remove the solvent, so that crude Z-L-valyl-L-valyl-(3S)-3-amino-2-oxo-pentanoyl-D-leucyl-L-valine benzyl ester was obtained as a partially gelled substance.

The crude product was purified by a thin layer chromatography (silica gel, dichloromethane:methanol (15:1) to obtain 63.2 mg of Z-L-valyl-L-valyl-(3S)-3-amino-2-oxo-pentanoyl-D-leucyl-L-valine benzyl ester as white crystals. Yield: 58.6%; mp.: 201.0°–202.0° C.; $[\alpha]_D^{26}+8.4°$; $[\alpha]_{436}^{26}+50.3°$ (c 0.90, chloroform).

$^1$H-NMR (CDCl$_3$)

δ 0.77–1.04(m, 27H, CH$_3$x9);
1.50–1.85(m, 4H, CH$_2$CH, CH$_3$-CH$_3$H$_b$);
2.00(m, 1H, CH$_3$-CH$_a$H$_b$);
2.05–2.25(m, 3H, CHx3(Val));
4.06(m, 1H, CH(Val));
4.32(dd, 1H, J=7.4 Hz, 8.6 Hz, CH(Val));
4.47–4.63(m, 2H, CH(Val), CH(Leu));
5.08, 5.16(d, d, 2H, J=12.0 Hz, CH$_2$-Ph);
5.10, 5.11(d, d, 2H, CH$_2$-Ph);
5.34(ddd, 1H, J=4.8, 8.2, 8.2 Hz, CH(EtAop));
5.57(br, d, 1H, J=8.6 Hz, NH(Val));
6.69(br, d, 1H, J=8.6 Hz, NH(Val));
6.74(br, d, 1H, J=9.1 Hz, NH(Val));
6.86(br, d, 1H, J=8.2 Hz, NH(EtAop));
7.25–7.40(m, 10H, Phx2);
7.48(br, d, 1H, J=8.8 Hz, NH(Leu)).

EXAMPLE 3

Synthesis of poststatin(L-valyl-L-valyl-(S)-3-amino-2-oxo-pentanoyl-D-leucyl-L-valyl) (compound 1)

46.9 mg (0.061 mmol) of Z-L-valyl-L-valyl-(S)-3-amino-2-oxo-pentanoyl-D-leucyl-L-valine benzyl ester were admixed with 6.6 mg of palladium black and 12 ml of methanol. The reaction mixture thus formed was subjected to a catalytic reduction reaction under a hydrogen atmosphere for 20.5 hours. After the catalyst has been filtered off, the filtrate was distilled to remove the solvent, so that 40.0 mg of a white crystalline material were obtained.

39.7 mg of the white material thus obtained were subjected to a HPLC operation (column: "CAPCELL PAK C$_{18}$", manufactured by SHISEIDO Co., Ltd., 20×250 mm; eluant:aqueous solution of 1% citric acid and 0.65% potassium acetate/acetonitrile (8:2); flow rate: 8 ml/min.; detection wave length: 254 nm), so that the aimed product was separated from the unreacted material and a partially epimerized substance, i.e., L-valyl-L-valyl-(R)-3-amino-2-oxo-pentanoyl-D-leucyl-L-valine. By this operation, a fraction, which contained L-valyl-L-valyl-(S)-3-amino-2-oxo-pentanoyl-D-leucyl-L-valine, was isolated. This fraction was concentrated at 25° C., and the concentrated solution was subjected to a treatment with a "CHP20" resin, then washed with water and an elution operation was effected with 80% methanol. The resultant eluate was distilled to remove the solvent therefrom, and dried by employing a vacuum pump overnight whereby 15.2 mg of poststatin were obtained as whitish powder.

From NMR data, it was found that the above-mentioned poststatin product contained an amount of impurities derived from the CHP20 resin. Therefore, 5.1 mg of the poststatin product were again subjected to a treatment with the CHP20, and to an elution operation with 55% aqueous methanol. The eluate solution was distilled to remove the solvent. The solid residue was separated by a decantation, washed with ether, and dried by employing a vacuum pump to obtain 2.4 mg of purified poststatin as white powder. Yield: 21.7%.

SI-MS: m/z 542(M+1+).

$^1$H-NMR (DMSO-d$_6$)

δ 0.70–0.95(m, 27H, CH$_3$×9);
1.40–1.67(m, 3H, CH$_a$H$_b$CH(Leu), CH$_3$-CH$_a$CH$_b$);
1.61(m, 1H, CH$_a$H$_b$CH(Leu));
1.76(m, 1H, CH$_3$-CH$_a$H$_b$);
1.86–2.10(m, 3H, CH(Val));
3.20(m, 1H, CH(Val));
4.06(m, 1H, CH(Val));
4.27(m, 1H, CH(Val));
4.95(m, 1H, CHCOCO);
7.98(br, d, 1H, J=8.4 Hz, NH(Val));
8.10(br, d, 1H, J=8.9 Hz, NH(Val));
8.36(d, 1H, J=6.6 Hz, NH(EtAop));
8.56(d, 1H, J=8.7 Hz, NH(Leu)).

Furthermore, a broad peak was observed in a position (δ) of 2.80–3.90, due to the presence of water (including amino and carboxyl radicals).

REFERENCE EXAMPLE 8

Synthesis of Z-D-leucyl-L-valine t-butyl ester 1.000 g (3.77 mmol) of Z-D-leucine, 0.719 g (3.43 mmol) of L-valine t-butyl ester hydrochloride and 0.927 g (6.00 mmol) of N-hydroxyl-benzotriazole were dissolved in 17 ml of dichloromethane. To the resulting solution were added 0.530 ml of triethylamine and 1.265 g (4.80 mmol) of 97% 1-ethyl-3-(3-dimethylaminopropyl)carbodiimide perchlorate under cooling with ice. The reaction mixture was stirred for 2 hours, and further stirred at room temperature for 14 hours. After the completion of the reaction, the reaction mixture was successively washed with 7 ml of a saturated aqueous sodium hydrogen carbonate solution, 7 ml of water, 7 ml of a 1% aqueous citric acid solution and 7 ml of water, dried over anhydrous sodium sulfate, and distilled to remove the solvent therefrom, whereby 1.932 g of crude Z-D-leucyl-L-valine t-butyl ester were obtained as oil.

Then the crude product was purified by a column chromatography (silica gel; dichloromethane:methanol (400:3)), so that 1.267 g of purified Z-D-leucyl-L-valine t-butyl ester were obtained. Yield: 87.9%; $[\alpha]_{436}^{28}$ +66.3°; $[\alpha]_D^{28}$ +31.1° (c 1.06, chloroform).

REFERENCE EXAMPLE 9

Synthesis of erythro(2R, 3R),(2S, 3S)-Z(OMe)-3-amino-2-hydroxy-pentanoyl-D-leucyl-L-valine t-butyl ester To 503.9 mg (1.198 mmol) of Z-D-leucyl-L-valine t-butyl ester were added 21.2 mg of palladium black and 5 ml of methanol. A catalytic reduction reaction was carried out in a hydrogen atmosphere at room temperature for 3 hours. The catalyst was separated off by filtration, and the filtrate was distilled to remove the solvent therefrom, so that D-leucyl-L-valine t-butyl ester was obtained as oil. This ester compound was admixed with 391.1 mg (1.318 mmol) of erythro(2R, 3R),(2S, 3S)-3-(p-methoxy-benzyloxycarbonyl)amino-2-hydroxy-pentanoic acid, 324.1 mg (2.399 mmol) of N-hydroxyl-benzotriazole and 8 ml of dichloromethane. The solution thus formed was admixed with 442.1 mg (1.677 mmol) of 97% 1-ethyl-3-(3-dimethylaminopropyl)carbodiimide perchlorate under cooling with ice, stirred for 2 hours, and further stirred at room temperature overnight. After the completion of the reaction, the reaction mixture was successively washed with 8 ml of a saturated aqueous sodium hydrogen carbonate solution, 8 ml of water, 8 ml of a 1% aqueous citric acid solution and 8 ml of water, dried over anhydrous sodium sulfate, and distilled to remove the solvent therefrom, so that 728.1 mg of crude erythro(2R, 3R), (2S, 3S)-Z(OMe)-3-amino-2-hydroxy-pentanoyl-D-leucyl-L-valine t-butyl ester were obtained as jelly. The crude product was purified by a column chromatography (silica gel, dichloromethane:methanol (100:1)) to obtain 666.6 mg of purified erythro(2R, 3R), (2S, 3S)-Z(OMe)-3-amino-2-hydroxypentanoyl-D-leucyl-L-valine t-butyl ester as a amorphous solid material. Yield: 98.4%.

SI-MS: m/z 566 (M+1+).

REFERENCE EXAMPLE 10

Synthesis of Z-L-phenylalanyl-(2RS, 3RS)-3-amino-2-hydroxypentanoyl-D-leucyl-L-valine t-butyl ester 340.9 mg (0.603 mmol) of erythro(2R, 3R), (2S, 3S)-Z(OMe)-3-amino-2-hydroxypentanoyl-D-leucyl-L-valine t-butyl ester were dissolved in 4 ml of methanol. To the resulting solution were added 50.7 ml of palladium black in such a manner that the total amount of this catalyst was divided into three portions, which were intermittently added to the solution at an interval of several hours. The catalytic reduction reaction was effected in a hydrogen atmosphere at room temperature for 32 hours. After the completion of the reaction, the catalyst was separated off by filtration, the filtrate was distilled to remove the solvent therefrom, so that erythro(2R, 3R), (2S, 3S)-3-amino-2-hydroxypentanoyl-D-leucyl-L-valine t-butyl ester was obtained.

A half amount of the ester compound thus produced was admixed with 100.8 mg (0.337 mmol) of Z-L-phenylalanine, 81.9 mg (0.606 mmol) of N-hydroxybenzotriazole and 10 ml of dichloromethane. The resulting solution was cooled with ice, and admixed with 111.3 mg (0.422 mmol) of 97% 1-ethyl-3-(3-dimethylaminopropyl)carbodiimide, stirred for 2 hours, and further stirred at room temperature for 18 hours. After 2.0 ml of DMF had been further added, the reaction mixture was stirred for 22.5 hours, successively washed with 9 ml of a saturated aqueous sodium hydrogen carbonate solution, 9 ml of water, 9 ml of a 1% aqueous citric acid solution and 9 ml of water, dried over anhydrous sodium sulfate, and distilled to remove the solvent, whereby 255.6 mg of crude Z-L-phenylalanyl-(2RS, 3RS)-3-amino-2-hydroxypentanoyl-D-leucyl-L-valine t-butyl ester were obtained as oil. The crude product was used in the next reaction step without any purification operation.

EXAMPLE 4

Synthesis of Z-L-phenylalanyl-(RS)-3-amino-2-oxopentanoyl-D-leucyl-L-valine t-butyl ester (compound 3)

255.6 mg of crude Z-L-phenylalanyl-(2RS, 3RS)-3-amino2-hydroxypentanoyl-D-leucyl-L-valine benzyl ester, shown in Reference Example 10, were admixed with 25.8 mg (0.134 mmol) of pyridine trifluoroacetate, 211.6 mg (0.803 mmol) of 97% 1-ethyl-3-(3-dimethylaminopropyl)carbodiimide perchlorate, 0.65 ml of DMSO and 2 ml of toluene. The solution thus obtained was stirred at room temperature for 20 hours. After the completion of the reaction, the reaction mixture with a yellow color was diluted with 6.5 ml of ethyl acetate, washed with 7 ml of water, dried over anhydrous sodium sulfate, and distilled to remove the solvent, so that 244.4 mg of crude Z-L-phenylalanyl-(RS)-3-amino-2-oxopentanoyl-D-leucyl-L-valine t-butyl ester were obtained as an amorphous solid. The crude product was purified by a column chromatography (silica gel, dichloromethane:methanol (100:1)) to obtain 113.7 mg of purified Z-L-phenylalanyl-(RS)-3-amino-2-oxopentanoyl-D-leucyl-L-valine t-butyl ester. Yield: 63.5%.

SI-MS: m/z 681 (M+1+).

EXAMPLE 5

Synthesis of Z-L-phenylalanyl-(RS)-3-amino-2-oxopentanoyl-D-leucyl-L-valine (compound 4)

105.9 mg (0.156 mmol) of Z-L-phenylalanyl-(RS)-3-amino-2-oxopentanoyl-D-leucyl-L-valine t-butyl ester were admixed with 2 ml of trifluoroacetic acid. The solution thus formed was stirred at room temperature for 90 minutes, and distilled to remove the solvent therefrom. Then 2 ml of toluene were added to the solution, which was then distilled to remove the solvent therefrom. The toluene addition/distillation operation was carried out twice to obtain 106.5 mg of crude Z-L-phenylalanyl-(RS)-3-amino-2-oxopentanoyl-D-leucyl-L-valine as an amorphous solid. The crude product was purified by a column chromatography ("LH-20", methanol). 70.5 mg of purified Z-L-phenylalanyl-(RS)-3-amino-2-oxopentanoyl-D-leucyl-L-valine were obtained as a partially amorphous and partially white crystalline substance. Yield: 72.6%.

SI-MS: m/z 625 (M+1+); 647 (M+Na+).

REFERENCE EXAMPLE 11

Synthesis of Z(OMe)-(2RS, 3RS)-3-amino-2-hydroxypentanoyl-D-leucine t-butyl ester 0.896 g (4.00 mmol) of D-leucine t-butyl ester hydrochloride were admixed with 1.309 g (4.40 mmol) of (2RS, 3RS)-3-(p-methoxy-benzyloxycarbonyl)amino-2-hydroxypentanoic acid, 1.081 g (8.00 mmol) of N-hydroxybenzotriazole and 20 ml of dichloromethane. The resulting solution was cooled with ice, and admixed with 0.62 ml (4.43 mmol) of triethylamine and 1.476 g (5.60 mmol) of 97% 1-ethyl-3-(3-dimethylaminopropyl)carbodiimide perchlorate. The reaction mixture was stirred for 2 hours, and further stirred at room temperature for 15 hours.

After the completion of the reaction, the reaction mixture was successively washed with 8 ml of a saturated aqueous sodium hydrogen carbonate solution, 8 ml of water, 8 ml of a 1% aqueous citric acid solution and 8 ml of water, dried over anhydrous sodium sulfate, and distilled to remove the solvent, so that 2.122 g of crude Z(OMe)-(2RS, 3RS)-3-amino-2-hydroxypentanoyl-D-leucine t-butyl ester were obtained as jelly. The crude product was purified by a column chromatography (silica gel, dichloromethane:methanol (100:1)) to obtain 1.858 g of purified Z(OMe)-(2RS, 3RS)-3-amino-2-hydroxypentanoyl-D-leucine t-butyl ester as white crystals. Yield: 99.6%. IS-MS: m/z 467 (M+1+).

REFERENCE EXAMPLE 12

Synthesis of Boc-L-valyl-(2RS, 3RS)-3-amino-2-hydroxypentanoyl-D-leucine t-butyl ester 303.9 mg (0.651 mmol) of erythro(2R, 3R), (2S, 3S)-Z(OMe)-3-amino-2-hydroxy-pentanoyl-D-leucine t-butyl ester were dissolved in 4 ml of methanol.

43.4 mg of palladium black were divided into three portions, which were intermittently added to the reaction mixture at an interval of several hours. The catalytic reduction reaction was effected in a hydrogen atmosphere at room temperature for 15 hours. Thereafter, the catalyst was separated off by filtration, and the filtrate was distilled to remove the solvent therefrom. Erythro(2R, 3R), (2S, 3S)-3-amino-2-hydroxypentanoyl-D-leucine t-butyl ester was obtained.

The ester compound thus formed was admixed with 155.9 mg (0.718 mmol) of Boc-L-valine, 176.1 mg (1.303 mmol) of N-hydroxyl-benzotriazole and 3.5 ml of dichloromethane. The resulting reaction mixture was cooled with ice, admixed with 499.4 mg (2.605 mmol) of 1-ethyl-3-(3-dimethylaminopropyl)carbodiimide hydrochloride, stirred for 2 hours, and further stirred at room temperature for 16.5 hours. The reaction mixture was diluted with 7 ml of dichloromethane, successively washed with 6 ml of a 1% aqueous citric acid solution, 6 ml of water, 6 ml of a saturated aqueous sodium hydrogen carbonate solution and 6 ml of water, dried over anhydrous sodium sulfate, and distilled to remove the solvent therefrom so that crude Boc-L-valyl-(2RS, 3RS)-3-amino-2 hydroxypentanoyl-D-leucine t-butyl ester was obtained as an amorphous material. The crude product was used in the next reaction step without a purification operation.

EXAMPLE 6

Synthesis of Boc-L-valyl-(RS)-3-amino-2-oxopentanoyl-D-leucine t-butyl ester (compound 5)

0.651 mmol of Boc-L-valyl-(2Rs, 3RS)-3-amino-2-hydroxypentanoyl-D-leucine t-butyl ester were admixed with 69.5 (0.360 mmol) of pyridine trifluoroacetate, 408.8 mg (1.982 mmol) of dicyclohexylcarbodiimide, 1.3 ml of DMSO and 2.5 ml of toluene. The reaction mixture was stirred at room temperature for 18 hours. After the completion of the reaction, the reaction mixture, having a yellow color, was diluted with 10 ml of ethyl acetate. Dicyclohexylurea thus formed was separated off by filtration. The organic layer was diluted with 10 ml of water, dried over anhydrous sodium sulfate, and distilled to remove the solvent therefrom, whereby an oily substance was obtained. The oily substance was admixed with 5 ml of ethyl acetate, whereby a further amount of dicyclohexylurea was crystallized and filtered off. The filtrate was distilled to remove the solvent therefrom, so that crude Boc-L-valyl-(RS)-3-amino-2-oxopentanoyl-D-leucyl t-butyl ester was obtained. The crude product was purified by a column chromatography (silica gel; and (1) dichloromethane:methanol (100:1), and (2) dichloromethane:ethyl acetate (12:1 to 10:1)) to obtain 178.2 mg of Boc-L-valyl-(RS)-3-amino-2-oxopentanoyl-D-leucyl t-butyl ester as white crystals. SI-MS: m/z 534 (M+1+).

REFERENCE EXAMPLE 13

Synthesis of (2R, 3S)-3-(9-fluorenylmethyloxycarbonyl)amino-2-hydroxypentanoic acid 0.759 g (5.70 mmol) of (2R, 3S)-3-amino-2-hydroxypentanoic acid were admixed with a solution of 1.199 g (14.28 mmol) of sodium hydrogen carbonate in 20 ml of water, and with 20 ml of dioxane. The resulting mixture was cooled with ice. To this solution was dropwise added a solution of 1.623 g (6.27 mmol) of 9-fluorenylmethyl chloroformate in 10 ml of dioxane under cooling with ice for 30 minutes. After the completion of the addition, the reaction mixture was stirred at room temperature for 2 hours, diluted with 100 ml of water, and successively washed with 150 ml of ether and 75 ml of ether. To the aqueous layer were added 2.8 ml of 6N hydrochloric acid to adjust to pH 1.5. Then the aqueous layer was extracted three times with 50 ml of ethyl acetate. The oil layer was washed with 50 ml of a saturated aqueous sodium chloride solution, dried over anhydrous sodium sulfate, and distilled to remove the solvent therefrom, so that 1.622 g of crude (2R, 3S)-3-(9-fluorenylmethoxycarbonyl)amino-2-hydroxypentanoic acid were obtained.

The crude product was admixed with 4 ml of ethyl acetate and 4 ml of n-hexane to form crystals, which were then separated by filtration, washed with 2 ml of an ethyl acetate/n-hexane (1:1) solution, and thereafter dried to obtain 0.999 g of (2R, 3S)-3-(9-fluorenylmethoxycarbonyl)amino-2-hydroxypentanoic acid as white crystals. mp.: 160°–161.5° C.

0.999 g of the protected amino acid thus obtained were admixed with 4 ml of ethyl acetate. The resulting suspension was stirred at 50° C. for 40 minutes, then admixed with 4 ml of n-hexane, and the crystals was separated by filtration. The crystals was washed with 2 ml of an ethyl acetate/n-hexane (1:1) solution, and dried to obtain 0.866 g of (2R, 3S)-3-(9-fluorenylmethoxycarbonyl)amino-2-hydroxypentanoic acid as white crystals. Recrystallization Yield: 86.7%.

$[\alpha]_D^{26} -30.2°$; $[\alpha]_{436}^{26} -63.0°$ c 1.01, methanol): mp. 162°–162.5° C.; FAB-MS; m/z 356 (M+1+).

$^1$H-NMR (CDCl$_3$)

δ 0.96(dd, 3H, J=7.4, 7.4 Hz, CH$_3$);
1.69(m, 2H, CH$_2$);
3.25(br, COOH, OH);
4.01(m, 1H, CHNH);
4.18(dd, 1H, J=6.6, 6.6 Hz, ArCHAr);
4.24(br, s, 1H, CHOH);
4.40, 4.41(d, d, 1H, 1H, J=6.6, 6.6 Hz, ArCH-HCH$_a$H$_b$);
5.13(d, 1H, J=9.6 Hz, NH);
7.20–7.80(m, 8H, Ar).

The filtrate and the washing liquid of the above-mentioned crystallization operation were distilled to obtain 0.548 g of an amorphous material, which was purified by a column chromatography (silica gel; chloroform::methanol:acetic acid (95:5:1)), to further obtain 0.307 g of (2R, 3S)-3-(9-fluorenylmethyloxycarbonyl)amino-2-hydroxypentanoic acid as white crystals.

REFERENCE EXAMPLE 14

Synthesis of Boc-L-Val-L-Val-L-3-amino-2-hydroxypentanoyl-D-Leu-L-val resin 0.5 g of Fmoc-L-valyl-p-alkoxybenzylalcohol resin (which contained 0.345 mmol of valine), were swelled in dimethyl formamide (3×6 ml, 1 minutes). This resin was a commercial product of Watanabe Chemical Co., Ltd.

The swelled resin was admixed with 6 ml of a 20% piperidine/DMF mixture, and the resulting mixture was stirred for 3 minutes. After the solvent had been removed, the above-mentioned piperidine treatment was twice repeated, with the proviso that the stirring was effected for 3 minutes and 20 minutes in the second treatment and the third treatment, respectively. After the solvent had been removed, the resin was washed with DMF (3×6 ml, 1 minute), and then with N-methylpyrrolidone (3×6 ml, 1 minute).

366 mg (3 equivalents) of Fmoc-D-Leu, 140 mg (3 equivalents) of HOBt and 0.265 ml (3 equivalents) of diisopropyl-carbodiimide were dissolved in 6 ml of N-methyl-pyrrolidone. The resultant solution was added to the resin, and stirred for 3 hours. After the removal of the solvent, the resin was washed in N-methylpyrrolidone (3×6 ml, 1 minute). Then the solvent was removed therefrom, and the resin was washed with DMF (3×6 ml, 1 minute).

Next, a piperidine treatment for the removal of the protective radicals was effected in the same manner as mentioned above. 368 mg of Fmoc-3-amino-2-hydroxypentanoic acid, 140 mg of HOBt and 0.265 ml (3 equivalents) of diisopropylcarbodiimide were dissolved in 6 ml of N-methylpyrrolidone. The resulting solution was added to the resin, and stirred for 3 hours. Then the resin was subjected to a washing operation, a piperidine deprotection operation and a further washing operation in the manner shown above. Thereafter, 351 mg of Fmoc-L-Val and 225 mg of Boc-L-Val were condensed with the resin in a manner similar to that stated above.

REFERENCE EXAMPLE 15

Oxidation of Boc-L-Val-L-Val-L-3-amino-2-hydroxypentanoyl-D-Leu-L-Val resin

The above mentioned resin was washed with DMF (3×6 ml, 1 minute) and then with DMSO (3×6 ml, 1 minute).

0.45 mg of pyridinium trifluoroacetate and 125 ml of acetic acid anhydride were dissolved in 6 ml of DMSO. The resulting solution was added to the resin, and stirred for 18 hour. After the removal of the solvent, the resin was successively washed with DMSO (3×6 ml, 1 minute), DMF (3×6 ml, 1 minute) and methanol (3×6 ml, 1 minute), and dried in vacuum for 2 hours.

EXAMPLE 7

Synthesis of poststatin(L-val-L-val-L-3-amino-2-oxo pentanoyl-D-Leu-L-val) (compound 1)

The dry resin, shown in Reference Example 15, was treated with TFA:phenol (95:5) (2×6 ml). The resulting solution was evaporated in vacuum, and the residue was dissolved in 3 ml of methanol. The methanol solution was supplied to a column filled with 30 ml of "Sephadex LH-20" which had been swelled in methanol. An elution operation was effected with methanol. Initial fractions, which showed UV absorption, were collected and evaporated in vacuum. The residue (139 mg) was dissolved in a mixture of n-butanol, acetic acid and water (100:1:100) in such a way that the residue was dissolved in 1 ml of the upper layer and in 1 ml of the layer of the mixture. A chromatography was effected in a centrifugal, counter current type chromatography apparatus (manufactured by Sanki Engineering Co., Ltd.), wherein the lower layer mentioned above was employed as mobile phase. Fractions, which showed UV absorption, were collected and evaporated in vacuum to obtain 82.9 mg of the title compound as colorless powder.

EXAMPLE 8

Synthesis of L-valyl-L-prolyl-3-amino-2-oxopentanoyl-D-leucyl-L-valine (compound 6)

A synthetic operation was carried out in a manner similar to that shown in Reference Examples 14 and 15 and in Example 7. As the starting material, use was made of 0.5 g of Fmoc-L-valyl resin. 3 equivalents of Fmoc-amino acids were successively subjected to the condensation reaction, the oxidation and the deprotection operations, so that 124.6 mg of L-valyl-L-prolyl-3-amino-2-oxopentanoyl-D-leucyl-L-valine were obtained.

EXAMPLE 9

Synthesis of phenylbutanoyl-L-valyl-L-propyl-3-amino-2-oxopentanoyl-D-leucyl-L-valine (compound 7)

23.6 mg of L-valyl-L-prolyl-3-amino-2-oxo-pentanoyl-D-leucyl-L-valine prepared by the manner shown in Example 8 were dissolved in 2 ml of methanol. The resultant solution was admixed with a solution of 30 mg of 4-phenyl-butanoic acid anhydride in 1 ml of methylene chloride and with 0.050 ml of triethylamine, and stirred at room temperature for 1 hour. The reaction mixture was acidified with acetic acid, and subjected to a purification operation by employing a column (300 ml) filled with "Sefadex LH$_{20}$" with methanol, so that 20.9 mg of phenylbutanoyl-L-valyl-L-prolyl-3-amino-2-oxopentanoyl-D-leucyl-L-valine were obtained.

EXAMPLE 10

A number of poststatin homologue compounds were synthesized in a manner similar to that shown in the above. These compounds are shown in Table 2. Compounds 8-17, 22 and 24-24 were prepared from the corresponding starting materials in a manner similar to that shown in Reference Examples 14 and 15 and in Example 7.

Compounds 18-21 were produced in a manner similar to that shown in Reference Examples 14 and 15 and in Examples 7-9.

Compound 27 was prepared in a manner similar to that shown in Reference Examples 1-7 and in Example 2.

The physical constants of these compounds are also given in Table 2.

TEST 1

Determination of anti-prolylendopeptidase activity

The determination of anti-prolylendopeptidase activity was conducted by a modified method based on the method by Yoshimoto et al (Biochim. Biophys. Acta, vol. 569, pages 184-192 (1979)).

A test tube was charged with a solution mixture consisting of (a) 0.2 ml of a solution of 0.5 mM N-benzyloxycarbonyl-L-glycyl-L-prolyl-beta-naphthylamide in 40% dioxane; (b) 0.5 ml of a 0.05M Tris-HCl buffer solution (pH 7.8); and (c) 0.25 ml of an aqueous solution containing the test material. The solution mixture was heated to 37° C. for 3 minutes, and admixed with 0.05 ml of a prolylendopeptidase solution to effect a reaction at 37° C. for 30 minutes. The prolylendopeptidase employed was that which had been obtained according to a modified method based on the enzyme purification method by Koida, Walter et al. (J. Biol. Chem. Vol. 251, pages 7593-7599 (1976), wherein a pig kidney sample was subjected to a fractionation operation with ammonium sulfate, and wherein a purification was effected by a column chromatography employing a DEAE-Sephadex A-50 column.

After the completion of the reaction, the reaction mixture was admixed with 1 ml of a 1M sodium acetate buffer solution containing 10% of Tween-20 and 0.1% of Fast Garnet GBC salt. The reaction mixture was allowed to stand at room temperature for 15 minutes, and then measured for the light absorption at 525 nm (a). At the same time, a control sample, which was free of the test compounds and contained only the buffer solution, was measured for the light absorption (b).

The prolylendopeptidase inhibition activity was determined by employing the formula:

$$[(b-a)/b] \times 100$$

The results of this test are given in Table 2.

TEST 2

Determination of elastase inhibition activity and cathepsin B inhibition activity The elastase inhibition activity was determined according to a method by Mumford, R. A. et al (J. Biol. Chem., 225, 2227 (1980)). The cathepsin B inhibition activity was determined according to a method by Knight, C. G. (Biochem. J., 189. 447-453 (1980)). The test results are given in Table 2.

EXAMPLE 11

Production of poststatin tablets 30 parts by weight of poststatin, 120 parts of crystalline lactose, 147 parts of crystalline cellulose and 3 parts of magnesium stearate were mixed in a V-shape mixer, and the resulting mixture was formulated into tablets, each of which had a weight of 300 mg.

TABLE 2

| Compound No. | Substituent X | R₁ | Configuration of carbon atom to which R₁ is bonded | Y |
|---|---|---|---|---|
| 1 | Val—Val | Et | S | D—Leu—Val |
| 2 | Z—Val—Val | Et | S | D—Leu—Val—OBzl |
| 3 | Z—Phe | Et | RS | D—Leu—Val—OBut |
| 4 | Z—Phe | Et | RS | D—Leu—Val |
| 5 | Boc—Val | Et | RS | D—Leu—OBut |
| 6 | Val—Pro | Et | RS | D—Leu—Val |
| 7 | PB—Val—Pro | Et | RS | D—Leu—Val |
| 8 | Z—Val—Val | Et | RS | L—Leu—Val |
| 9 | Val—Val | Et | RS | L—Leu—Val |
| 10 | Val—Val | Et | RS | Gly—Val |
| 11 | Val—Val | Bz | RS | D—Leu—Val |
| 12 | Z—Val—Pro | Et | RS | D—Leu—Val |
| 13 | Val—Val | Me | RS | D—Leu—Val |
| 14 | Z—Val—Val | Me | RS | D—Leu—Val |
| 15 | Z—Val—Val | Et | RS | D—Leu—Val |
| 16 | Z—Val | Et | RS | D—Leu—Val |
| 17 | Z—Pro | Et | RS | D—Leu—Val |
| 18 | PB—Val—Val | Et | RS | D—Leu—Val |
| 19 | BZ—Val—Val | Et | RS | D—Leu—Val |
| 20 | PA—Val—Val | Et | RS | D—Leu—Val |
| 21 | PP—Val—Val | Et | RS | D—Leu—Val |
| 22 | Val—Val | Pr | RS | D—Leu—Val |
| 23 | Z—Val—Val | Et | RS | D—Leu—Val—OMe |
| 24 | Z—Lys—Val | Et | S | D—Leu—Val |
| 25 | Val—Thr | Et | RS | D—Leu—Val |
| 26 | Z—Asp—Val | Et | RS | D—Leu—Val |
| 27 | Z—Val | Et | RS | D—Leu—Val—OBzl |

| Compound No. | Physical constant Rf1 | Rf2 | Rf3 | Rf4 | MS | Endopeptidase inhibition activity PPCE | Elast. | Cat-B |
|---|---|---|---|---|---|---|---|---|
| 1 | 0.54 |  | 0.70 | 0.08 | 542 (M+1) | 0.03 | 110 | 2.1 |
| 2 | 0.01 |  | 0.97 | 0.92 | 566 (M+1) | 1 | 75 | 100 |
| 3 | 0.01 |  | 0.99 | 0.75 | 681 (M+1) | 0.11 | 50 | >100 |
| 4 | 0.35 |  | 0.97 | 0.65 | 625 (M+1) | 0.007 | 40 | 0.64 |
| 5 | 0.03 |  | 0.99 | 0.85 | 500 (M+1) | 0.04 | 5 | 2.2 |
| 6 | 0.49 | 0.53 | 0.56 | 0.04 | 540 (M+1) | 0.3 | 115 | >100 |
| 7 | 0.36 |  | 0.97 | 0.66 | 668 (M+1) | 0.17 | 0.9 | 72 |
| 8 | 0.34 |  | 0.99 | 0.69 | 676 (M+1) | 2.2 | 4 | 0.03 |
| 9 | 0.52 | 0.55 | 0.8 | 0.08 | 542 (M+1) | 12 | >100 | 0.04 |
| 10 | 0.61 | 0.65 | 0.61 | 0.03 | 486 (M+1) | 1.3 | >100 | 0.3 |
| 11 | 0.47 | 0.51 | 0.82 | 0.14 | 614 (M+1) | >100 | 90 | 0.5 |
| 12 | 0.37 |  | 0.97 | 0.64 | 674 (M+1) | 0.05 | 2.5 | >100 |
| 13 | 0.51 | 0.55 | 0.73 | 0.05 | 528 (M+1) | 0.05 | >100 | 9 |
| 14 | 0.39 |  | 0.97 | 0.62 | 662 (M+1) | 0.03 | 40 | 4.2 |
| 15 | 0.32 |  | 0.95 | 0.64 | 676 (M+1) | 0.034 | 5 | 1.1 |
| 16 | 0.46 |  | 0.95 | 0.72 | 577 (M+1) | 0.065 | >100 | 1.4 |
| 17 | 0.45 |  | 0.97 | 0.7 | 575 (M+1) | 0.02 | >100 | 120 |
| 18 | 0.36 |  | 0.98 | 0.67 | 688 (M+1) | 0.04 | 1.5 | 1.1 |
| 19 | 0.45 |  | 0.97 | 0.65 | 646 (M+1) | 0.07 | 7.5 | 1.4 |
| 20 | 0.38 |  | 0.97 | 0.59 | 660 (M+1) | 0.022 | >100 | 1.5 |
| 21 | 0.44 |  | 0.98 | 0.61 | 674 (M+1) | 0.025 | >100 | 2.1 |
| 22 | 0.52 | 0.55 | 0.73 | 0.07 | 555 (M+1) | 0.38 | >100 | 1.4 |
| 23 | 0.06 |  | 0.97 | 0.72 | 690 (M+1) | 0.34 | 25 | 92 |
| 24 | 0.44 |  | 0.67 | 0.05 | 705 (M+1) | 0.03 | 15 | 0.65 |
| 25 | 0.53 | 0.55 | 0.58 | 0.03 | 544 (M+1) | 0.27 | >100 | 8.5 |
| 26 | 0.46 |  | 0.93 | 0.28 | 691 (M+1) | 0.39 | 13 | 6.3 |
| 27 | 0.01 |  | 0.99 | 0.76 | 667 (M+1) | 0.05 | >100 | >100 |

Remarks*
The abbreviations, employed in Table 2, have the meanings shown below.
Rf1, Rf2 = TLC, reverse phase (RP-18), "5% KOAc-1% citric acid":"MeCN" = 65:35;
Rf3 = TLC, silica gel F, n-BuOH:AcOH:H₂O = 4:1:1;
Rf4 = TLC, silica gel F, CHCl₃:MeOH:AcOH = 90:10:5;
PPCE = Proplyendopeptidase inhibition activity, IC₅₀ (μg/ml);
Elast = Elastase inhibition activity, IC₅₀ (μg/ml);
Cat-B = Cathepsin B inhibition activity, IC₅₀ (μg/ml).

INDUSTRIAL UTILITY

Poststatin and homologue compounds or salts thereof according to the invention exhibit a high endopeptidase inhibition activity. So, these compounds are useful as medicines for treating amnesia, and auto-immunization diseases such as systemic erythematosus and the like.

We claim:

1. Poststatin and related compounds or salts thereof having the formula:

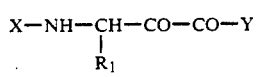     [I]

wherein X represents an amino acid residue having any one of the formulas (a) to (c), with the proviso that the amino radicals contained in the amino acid residue may optionally be present in the protected form:

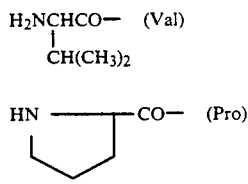 (a)

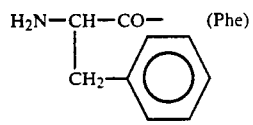 (b)

H₂N—CH—CO—  (Phe) (c)
|
CH₂—⬡ or X represents a peptide residue having any one of the formulas (d) to (h), with the proviso that the functional radicals contained in the peptide residue may optionally be present in the protected form

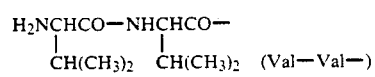 (d)

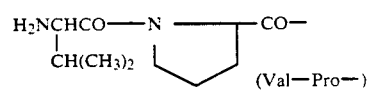 (e)

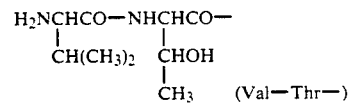 (f)

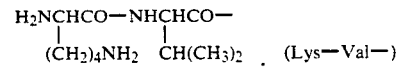 (g)

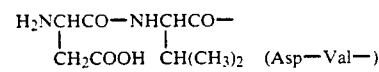 (h)

R₁ represents lower alkyl or benzyl; and Y represents an amino acid residue having the formula (i) with the proviso that the carboxyl radicals contained in the amino acid residue may optionally be present in the protected form, or Y represents a peptide residue having any one of the formulas (j) to (k), with the proviso that the functional radicals contained in the peptide residue may optionally be present in the protected form:

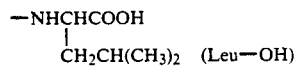 (i)

-continued

—NHCHCO————NHCHCOOH        (j)
|                |
CH₂CH(CH₃)₂    CH(CH₃)₂   (—Leu—Val—OH)

—NHCH₂CO—NHCHCOOH          (k)
               |
              CH(CH₃)₂  (Gly—Val—OH)

2. Poststatin and related compounds or salts thereof as defined in claim 1, wherein X given in the formula (I) represents a radical having terminal amino radicals optionally protected, and having the formula:

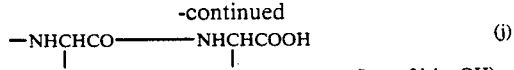

R₁ is ethyl, and Y represents a radical having terminal carboxyl radicals optionally protected as ester moieties, and having any of the formulas:

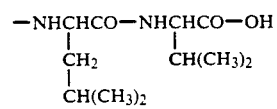

(—D—Leu—Val—OH);

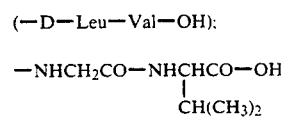

(Gly—Val—OH).

3. Poststatin and ester compounds or salts thereof having the formula:

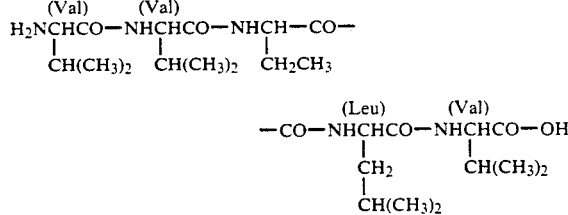

with the proviso that the amino radicals contained in the compound may optionally be present in the protected form.

4. Poststatin related compound or ester or salt thereof having the formula:

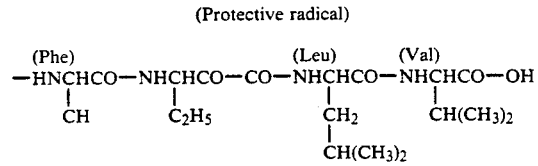

* * * * *